United States Patent
Ranpura et al.

(10) Patent No.: US 10,258,428 B2
(45) Date of Patent: Apr. 16, 2019

(54) MARKER DELIVERY DEVICE FOR TISSUE MARKER PLACEMENT

(71) Applicant: C. R. Bard, Inc., Tempe, AZ (US)

(72) Inventors: Himanshu Ranpura, Stevenson Ranch, CA (US); Chad C. Van Liere, Phoenix, AZ (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 1202 days.

(21) Appl. No.: 14/202,842

(22) Filed: Mar. 10, 2014

(65) Prior Publication Data

US 2014/0194892 A1    Jul. 10, 2014

Related U.S. Application Data

(63) Continuation of application No. 12/595,010, filed as application No. PCT/US2008/088558 on Dec. 30, 2008, now Pat. No. 8,670,818.

(51) Int. Cl.
*A61B 5/05* (2006.01)
*A61B 6/00* (2006.01)
*A61B 90/00* (2016.01)

(52) U.S. Cl.
CPC ...... *A61B 90/39* (2016.02); *A61B 2090/3987* (2016.02)

(58) Field of Classification Search
None
See application file for complete search history.

(56) References Cited

U.S. PATENT DOCUMENTS 2,481,408 A    9/1949  Fuller et al.
2,899,362 A    8/1959  Sieger, Jr. et al.
(Continued)

FOREIGN PATENT DOCUMENTS

DE    1029528 B     5/1958
EP    0146699 A1    7/1985
(Continued)

OTHER PUBLICATIONS

Armstong, J.S., et al., "Differential marking of Excision Planes in Screened Breast lesions by Organically Coloured Gelatins", Journal of Clinical Pathology, Jul. 1990, No. 43 (7) pp. 604-607, XP000971447 abstract; tables 1,2.

(Continued)

*Primary Examiner* — Patricia J Park

(57) ABSTRACT

A marker delivery device is configured for deploying a tissue marker. The marker delivery device includes a handle having a chamber, and a cannula. According to one aspect, the cannula has a flexible portion formed by a slot arrangement having of a plurality of spaced-apart substantially parallel peripheral slots extending through the side wall of the cannula to the lumen. A marker introducer rod is movably disposed in the lumen of the cannula for deploying the mark, and has a flexible region that corresponds to the flexible portion of the cannula. According to another aspect, a retraction mechanism is mounted to the handle and is configured to facilitate a complete retraction of both the cannula and the marker introducer rod into the chamber of the housing of the handle upon an actuation of the retraction mechanism.

3 Claims, 13 Drawing Sheets

(56) References Cited

U.S. PATENT DOCUMENTS

| | | |
|---|---|---|
| 2,907,327 A | 10/1959 | White |
| 3,005,457 A | 10/1961 | Millman |
| 3,128,744 A | 4/1964 | Jefferts et al. |
| 3,341,417 A | 9/1967 | Sinaiko |
| 3,402,712 A | 9/1968 | Eisenhand |
| 3,516,412 A | 6/1970 | Ackerman |
| 3,593,343 A | 7/1971 | Viggers |
| 3,757,781 A | 9/1973 | Smart |
| 3,818,894 A | 6/1974 | Wichterle et al. |
| 3,820,545 A | 6/1974 | Jefferts |
| 3,823,212 A | 7/1974 | Chvapil |
| 3,921,632 A | 11/1975 | Bardani |
| 4,005,699 A | 2/1977 | Bucalo |
| 4,007,732 A | 2/1977 | Kvavle et al. |
| 4,041,931 A | 8/1977 | Elliott et al. |
| 4,086,914 A | 5/1978 | Moore |
| 4,103,690 A | 8/1978 | Harris |
| 4,105,030 A | 8/1978 | Kercso |
| 4,127,774 A | 11/1978 | Gillen |
| 4,172,449 A | 10/1979 | LeRoy et al. |
| 4,197,846 A | 4/1980 | Bucalo |
| 4,217,889 A | 8/1980 | Radovan et al. |
| 4,276,885 A | 7/1981 | Tickner et al. |
| 4,294,241 A | 10/1981 | Miyata |
| 4,298,998 A | 11/1981 | Naficy |
| 4,331,654 A | 5/1982 | Morris |
| 4,347,234 A | 8/1982 | Wahlig et al. |
| 4,390,018 A | 6/1983 | Zukowski |
| 4,400,170 A | 8/1983 | McNaughton et al. |
| 4,401,124 A | 8/1983 | Guess et al. |
| 4,405,314 A | 9/1983 | Cope |
| 4,428,082 A | 1/1984 | Naficy |
| 4,438,253 A | 3/1984 | Casey et al. |
| 4,442,843 A | 4/1984 | Rasor et al. |
| 4,470,160 A | 9/1984 | Cavon |
| 4,487,209 A | 12/1984 | Mehl |
| 4,545,367 A | 10/1985 | Tucci |
| 4,549,560 A | 10/1985 | Andis |
| 4,582,061 A | 4/1986 | Fry |
| 4,582,640 A | 4/1986 | Smestad et al. |
| 4,588,395 A | 5/1986 | Lemelson |
| 4,597,753 A | 7/1986 | Turley |
| 4,647,480 A | 3/1987 | Ahmed |
| 4,655,226 A | 4/1987 | Lee |
| 4,661,103 A | 4/1987 | Harman |
| 4,682,606 A | 7/1987 | DeCaprio |
| 4,693,237 A | 9/1987 | Hoffman et al. |
| 4,718,433 A | 1/1988 | Feinstein |
| 4,740,208 A | 4/1988 | Cavon |
| 4,762,128 A | 8/1988 | Rosenbluth |
| 4,813,062 A | 3/1989 | Gilpatrick |
| 4,820,267 A | 4/1989 | Harman |
| 4,832,680 A | 5/1989 | Haber et al. |
| 4,832,686 A | 5/1989 | Anderson |
| 4,847,049 A | 7/1989 | Yamamoto |
| 4,863,470 A | 9/1989 | Carter |
| 4,870,966 A | 10/1989 | Dellon et al. |
| 4,874,376 A | 10/1989 | Hawkins, Jr. |
| 4,889,707 A | 12/1989 | Day et al. |
| 4,909,250 A | 3/1990 | Smith |
| 4,931,059 A | 6/1990 | Markham |
| 4,938,763 A | 7/1990 | Dunn et al. |
| 4,950,234 A | 8/1990 | Fujioka et al. |
| 4,950,665 A | 8/1990 | Floyd |
| 4,963,150 A | 10/1990 | Brauman |
| 4,970,298 A | 11/1990 | Silver et al. |
| 4,989,608 A | 2/1991 | Ratner |
| 4,994,013 A | 2/1991 | Suthanthiran et al. |
| 4,994,028 A | 2/1991 | Leonard et al. |
| 5,012,818 A | 5/1991 | Joishy |
| 5,013,090 A | 5/1991 | Matsuura |
| 5,018,530 A | 5/1991 | Rank et al. |
| 5,035,891 A | 7/1991 | Runkel et al. |
| 5,059,197 A | 10/1991 | Urie et al. |
| 5,081,997 A | 1/1992 | Bosley, Jr. et al. |
| 5,108,421 A | 4/1992 | Fowler |
| 5,120,802 A | 6/1992 | Mares et al. |
| 5,125,413 A | 6/1992 | Baran |
| 5,137,928 A | 8/1992 | Erbel et al. |
| 5,141,748 A | 8/1992 | Rizzo |
| 5,147,295 A | 9/1992 | Stewart |
| 5,147,307 A | 9/1992 | Gluck |
| 5,147,631 A | 9/1992 | Glajch et al. |
| 5,162,430 A | 11/1992 | Rhee et al. |
| 5,163,896 A | 11/1992 | Suthanthiran et al. |
| 5,195,540 A | 3/1993 | Shiber |
| 5,197,482 A | 3/1993 | Rank et al. |
| 5,197,846 A | 3/1993 | Uno et al. |
| 5,199,441 A | 4/1993 | Hogle |
| 5,201,704 A | 4/1993 | Ray |
| 5,219,339 A | 6/1993 | Saito |
| 5,221,269 A | 6/1993 | Miller et al. |
| 5,231,615 A | 7/1993 | Endoh |
| 5,234,426 A | 8/1993 | Rank et al. |
| 5,236,410 A | 8/1993 | Granov et al. |
| 5,242,759 A | 9/1993 | Hall |
| 5,250,026 A | 10/1993 | Ehrlich et al. |
| 5,271,961 A | 12/1993 | Mathiowitz et al. |
| 5,273,532 A | 12/1993 | Niezink et al. |
| 5,280,788 A | 1/1994 | Janes et al. |
| 5,281,197 A | 1/1994 | Arias et al. |
| 5,281,408 A | 1/1994 | Unger |
| 5,282,781 A | 2/1994 | Liprie |
| 5,284,479 A | 2/1994 | de Jong |
| 5,289,831 A | 3/1994 | Bosley |
| 5,290,310 A | 3/1994 | Makower et al. |
| 5,312,435 A | 5/1994 | Nash et al. |
| 5,320,100 A | 6/1994 | Herweck et al. |
| 5,320,613 A | 6/1994 | Houge et al. |
| 5,328,955 A | 7/1994 | Rhee et al. |
| 5,334,216 A | 8/1994 | Vidal et al. |
| 5,334,381 A | 8/1994 | Unger |
| 5,344,640 A | 9/1994 | Deutsch et al. |
| 5,353,804 A | 10/1994 | Kornberg et al. |
| 5,354,623 A | 10/1994 | Hall |
| 5,358,514 A | 10/1994 | Schulman et al. |
| 5,360,416 A | 11/1994 | Ausherman et al. |
| 5,366,756 A | 11/1994 | Chesterfield et al. |
| 5,368,030 A | 11/1994 | Zinreich et al. |
| 5,388,588 A | 2/1995 | Nabai et al. |
| 5,394,875 A | 3/1995 | Lewis et al. |
| 5,395,319 A | 3/1995 | Hirsch et al. |
| 5,405,402 A | 4/1995 | Dye et al. |
| 5,409,004 A | 4/1995 | Sloan |
| 5,417,708 A | 5/1995 | Hall et al. |
| 5,422,730 A | 6/1995 | Barlow et al. |
| 5,425,366 A | 6/1995 | Reinhardt et al. |
| 5,431,639 A | 7/1995 | Shaw |
| 5,433,204 A | 7/1995 | Olson |
| 5,449,560 A | 9/1995 | Antheunis et al. |
| 5,451,406 A | 9/1995 | Lawin et al. |
| 5,458,643 A | 10/1995 | Oka et al. |
| 5,460,182 A | 10/1995 | Goodman et al. |
| 5,469,847 A | 11/1995 | Zinreich et al. |
| 5,475,052 A | 12/1995 | Rhee et al. |
| 5,490,521 A | 2/1996 | Davis et al. |
| 5,494,030 A | 2/1996 | Swartz et al. |
| 5,499,989 A | 3/1996 | LaBash |
| 5,507,807 A | 4/1996 | Shippert |
| 5,508,021 A | 4/1996 | Grinstaff et al. |
| 5,514,085 A | 5/1996 | Yoon |
| 5,522,896 A | 6/1996 | Prescott |
| 5,538,726 A | 7/1996 | Order |
| 5,542,915 A | 8/1996 | Edwards et al. |
| 5,545,180 A | 8/1996 | Le et al. |
| 5,549,560 A | 8/1996 | Van de Wijdeven |
| 5,567,413 A | 10/1996 | Klaveness et al. |
| RE35,391 E | 12/1996 | Brauman |
| 5,580,568 A | 12/1996 | Greff et al. |
| 5,585,112 A | 12/1996 | Unger et al. |
| 5,611,352 A | 3/1997 | Kobren et al. |
| 5,626,611 A | 5/1997 | Liu et al. |
| 5,628,781 A | 5/1997 | Williams et al. |
| 5,629,008 A | 5/1997 | Lee |

(56) References Cited

U.S. PATENT DOCUMENTS

| | | |
|---|---|---|
| 5,636,255 A | 6/1997 | Ellis |
| 5,643,246 A | 7/1997 | Leeb et al. |
| 5,646,146 A | 7/1997 | Faarup et al. |
| 5,657,366 A | 8/1997 | Nakayama |
| 5,665,092 A | 9/1997 | Mangiardi et al. |
| 5,667,767 A | 9/1997 | Greff et al. |
| 5,669,882 A | 9/1997 | Pyles |
| 5,673,841 A | 10/1997 | Schulze et al. |
| 5,676,146 A | 10/1997 | Scarborough |
| 5,676,925 A | 10/1997 | Klaveness et al. |
| 5,688,490 A | 11/1997 | Tournier et al. |
| 5,690,120 A | 11/1997 | Jacobsen et al. |
| 5,695,480 A | 12/1997 | Evans et al. |
| 5,702,128 A | 12/1997 | Maxim et al. |
| 5,702,682 A | 12/1997 | Thompson |
| 5,702,716 A | 12/1997 | Dunn et al. |
| 5,716,981 A | 2/1998 | Hunter et al. |
| 5,747,060 A | 5/1998 | Sackler et al. |
| 5,749,887 A | 5/1998 | Heske et al. |
| 5,752,974 A | 5/1998 | Rhee et al. |
| 5,762,903 A | 6/1998 | Park et al. |
| 5,769,086 A | 6/1998 | Ritchart et al. |
| 5,776,496 A | 7/1998 | Violante et al. |
| 5,779,647 A | 7/1998 | Chau et al. |
| 5,782,764 A | 7/1998 | Werne |
| 5,782,771 A | 7/1998 | Hussman |
| 5,782,775 A | 7/1998 | Milliman et al. |
| 5,795,308 A | 8/1998 | Russin |
| 5,799,099 A | 8/1998 | Wang et al. |
| 5,800,362 A | 9/1998 | Kobren et al. |
| 5,800,389 A | 9/1998 | Burney et al. |
| 5,800,445 A | 9/1998 | Ratcliff et al. |
| 5,800,541 A | 9/1998 | Rhee et al. |
| 5,810,884 A | 9/1998 | Kim |
| 5,817,022 A | 10/1998 | Vesely |
| 5,820,918 A | 10/1998 | Ronan et al. |
| 5,821,184 A | 10/1998 | Haines et al. |
| 5,823,198 A | 10/1998 | Jones et al. |
| 5,824,042 A | 10/1998 | Lombardi et al. |
| 5,824,081 A | 10/1998 | Knapp et al. |
| 5,826,776 A | 10/1998 | Schulze et al. |
| 5,830,178 A | 11/1998 | Jones et al. |
| 5,830,222 A | 11/1998 | Makower |
| 5,842,477 A | 12/1998 | Naughton et al. |
| 5,842,999 A | 12/1998 | Pruitt et al. |
| 5,845,646 A | 12/1998 | Lemelson |
| 5,846,220 A | 12/1998 | Elsberry |
| 5,851,508 A | 12/1998 | Greff et al. |
| 5,853,366 A | 12/1998 | Dowlatshahi |
| 5,865,806 A | 2/1999 | Howell |
| 5,869,080 A | 2/1999 | McGregor et al. |
| 5,871,501 A | 2/1999 | Leschinsky et al. |
| 5,876,340 A | 3/1999 | Tu et al. |
| 5,879,357 A | 3/1999 | Heaton et al. |
| 5,891,558 A | 4/1999 | Bell et al. |
| 5,897,507 A | 4/1999 | Kortenbach et al. |
| 5,902,310 A | 5/1999 | Foerster et al. |
| 5,911,705 A | 6/1999 | Howell |
| 5,916,164 A | 6/1999 | Fitzpatrick et al. |
| 5,921,933 A | 7/1999 | Sarkis et al. |
| 5,922,024 A | 7/1999 | Janzen et al. |
| 5,928,626 A | 7/1999 | Klaveness et al. |
| 5,928,773 A | 7/1999 | Andersen |
| 5,941,439 A | 8/1999 | Kammerer et al. |
| 5,941,890 A | 8/1999 | Voegele et al. |
| 5,942,209 A | 8/1999 | Leavitt et al. |
| 5,948,425 A | 9/1999 | Janzen et al. |
| 5,954,670 A | 9/1999 | Baker |
| 5,972,817 A | 10/1999 | Haines et al. |
| 5,976,146 A | 11/1999 | Ogawa et al. |
| 5,980,564 A | 11/1999 | Stinson |
| 5,989,265 A | 11/1999 | Bouquet De La Joliniere et al. |
| 6,015,541 A | 1/2000 | Greff et al. |
| 6,030,333 A | 2/2000 | Sioshansi et al. |
| 6,053,925 A | 4/2000 | Barnhart |
| 6,056,700 A | 5/2000 | Burney et al. |
| 6,066,122 A | 5/2000 | Fisher |
| 6,066,325 A | 5/2000 | Wallace et al. |
| 6,071,301 A | 6/2000 | Cragg et al. |
| 6,071,310 A | 6/2000 | Picha et al. |
| 6,071,496 A | 6/2000 | Stein et al. |
| 6,090,996 A | 7/2000 | Li |
| 6,096,065 A | 8/2000 | Crowley |
| 6,096,070 A | 8/2000 | Ragheb et al. |
| 6,106,473 A | 8/2000 | Violante et al. |
| 6,117,108 A | 9/2000 | Woehr et al. |
| 6,120,536 A | 9/2000 | Ding et al. |
| 6,135,993 A | 10/2000 | Hussman |
| 6,142,955 A | 11/2000 | Farascioni et al. |
| 6,159,240 A | 12/2000 | Sparer et al. |
| 6,159,445 A | 12/2000 | Klaveness et al. |
| 6,161,034 A | 12/2000 | Burbank et al. |
| 6,162,192 A | 12/2000 | Cragg et al. |
| 6,166,079 A | 12/2000 | Follen et al. |
| 6,173,715 B1 | 1/2001 | Sinanan et al. |
| 6,174,330 B1 | 1/2001 | Stinson |
| 6,177,062 B1 | 1/2001 | Stein et al. |
| 6,181,960 B1 | 1/2001 | Jensen et al. |
| 6,183,497 B1 | 2/2001 | Sing et al. |
| 6,190,350 B1 | 2/2001 | Davis et al. |
| 6,190,353 B1 | 2/2001 | Makower et al. |
| 6,200,258 B1 | 3/2001 | Slater et al. |
| 6,203,507 B1 | 3/2001 | Wadsworth et al. |
| 6,203,524 B1 | 3/2001 | Burney et al. |
| 6,203,568 B1 | 3/2001 | Lombardi et al. |
| 6,213,957 B1 | 4/2001 | Milliman et al. |
| 6,214,045 B1 | 4/2001 | Corbitt, Jr. et al. |
| 6,214,315 B1 | 4/2001 | Greff et al. |
| 6,220,248 B1 | 4/2001 | Voegele et al. |
| 6,224,630 B1 | 5/2001 | Bao et al. |
| 6,228,049 B1 | 5/2001 | Schroeder et al. |
| 6,228,055 B1 | 5/2001 | Foerster et al. |
| 6,231,615 B1 | 5/2001 | Preissman |
| 6,234,177 B1 | 5/2001 | Barsch |
| 6,241,687 B1 | 6/2001 | Voegele et al. |
| 6,241,734 B1 | 6/2001 | Scribner et al. |
| 6,251,135 B1 | 6/2001 | Stinson et al. |
| 6,251,418 B1 | 6/2001 | Ahem et al. |
| 6,261,243 B1 | 7/2001 | Burney et al. |
| 6,261,302 B1 | 7/2001 | Voegele et al. |
| 6,264,917 B1 | 7/2001 | Klaveness et al. |
| 6,270,464 B1 | 8/2001 | Fulton, III et al. |
| 6,270,472 B1 | 8/2001 | Antaki et al. |
| 6,287,278 B1 | 9/2001 | Woehr et al. |
| 6,287,332 B1 | 9/2001 | Bolz et al. |
| 6,289,229 B1 | 9/2001 | Crowley |
| 6,306,154 B1 | 10/2001 | Hudson et al. |
| 6,312,429 B1 | 11/2001 | Burbank et al. |
| 6,316,522 B1 | 11/2001 | Loomis et al. |
| 6,325,789 B1 | 12/2001 | Janzen et al. |
| 6,335,029 B1 | 1/2002 | Kamath et al. |
| 6,336,904 B1 | 1/2002 | Nikolchev |
| 6,340,367 B1 | 1/2002 | Stinson et al. |
| 6,343,227 B1 | 1/2002 | Crowley |
| 6,347,240 B1 | 2/2002 | Foley et al. |
| 6,347,241 B2 | 2/2002 | Burbank et al. |
| 6,350,244 B1 | 2/2002 | Fisher |
| 6,350,274 B1 | 2/2002 | Li |
| 6,354,989 B1 | 3/2002 | Nudeshima |
| 6,356,112 B1 | 3/2002 | Tran et al. |
| 6,356,782 B1 | 3/2002 | Sirimanne et al. |
| 6,358,217 B1 | 3/2002 | Bourassa |
| 6,363,940 B1 | 4/2002 | Krag |
| 6,371,904 B1 | 4/2002 | Sirimanne et al. |
| 6,394,965 B1 | 5/2002 | Klein |
| 6,403,758 B1 | 6/2002 | Loomis |
| 6,405,733 B1 | 6/2002 | Fogarty et al. |
| 6,409,742 B1 | 6/2002 | Fulton, III et al. |
| 6,419,621 B1 | 7/2002 | Sioshansi et al. |
| 6,424,857 B1 | 7/2002 | Henrichs et al. |
| 6,425,903 B1 | 7/2002 | Voegele |
| 6,427,081 B1 | 7/2002 | Burbank et al. |
| 6,436,030 B2 | 8/2002 | Rehil |
| 6,447,524 B1 | 9/2002 | Knodel et al. |

(56) References Cited

U.S. PATENT DOCUMENTS

| | | |
|---|---|---|
| 6,447,527 B1 | 9/2002 | Thompson et al. |
| 6,450,937 B1 | 9/2002 | Mercereau et al. |
| 6,450,938 B1 | 9/2002 | Miller |
| 6,471,700 B1 | 10/2002 | Burbank et al. |
| 6,478,790 B2 | 11/2002 | Bardani |
| 6,506,156 B1 | 1/2003 | Jones et al. |
| 6,511,468 B1 | 1/2003 | Cragg et al. |
| 6,537,193 B1 | 3/2003 | Lennox |
| 6,540,981 B2 | 4/2003 | Klaveness et al. |
| 6,544,185 B2 | 4/2003 | Montegrande |
| 6,544,231 B1 | 4/2003 | Palmer et al. |
| 6,544,269 B2 | 4/2003 | Osborne et al. |
| 6,551,253 B2 | 4/2003 | Worm et al. |
| 6,554,760 B2 | 4/2003 | Lamoureux et al. |
| 6,562,317 B2 | 5/2003 | Greff et al. |
| 6,564,806 B1 | 5/2003 | Fogarty et al. |
| 6,565,551 B1 | 5/2003 | Jones et al. |
| 6,567,689 B2 | 5/2003 | Burbank et al. |
| 6,575,888 B2 | 6/2003 | Zamora et al. |
| 6,575,991 B1 | 6/2003 | Chesbrough et al. |
| 6,585,773 B1 | 7/2003 | Xie |
| 6,605,047 B2 | 8/2003 | Zarins et al. |
| 6,610,026 B2 | 8/2003 | Cragg et al. |
| 6,613,002 B1 | 9/2003 | Clark et al. |
| 6,616,630 B1 | 9/2003 | Woehr et al. |
| 6,626,850 B1 | 9/2003 | Chau et al. |
| 6,626,899 B2 | 9/2003 | Houser et al. |
| 6,628,982 B1 | 9/2003 | Thomas et al. |
| 6,629,947 B1 | 10/2003 | Sahatjian et al. |
| 6,636,758 B2 | 10/2003 | Sanchez et al. |
| 6,638,234 B2 | 10/2003 | Burbank et al. |
| 6,638,308 B2 | 10/2003 | Corbitt, Jr. et al. |
| 6,652,442 B2 | 11/2003 | Gatto |
| 6,656,192 B2 | 12/2003 | Espositio et al. |
| 6,659,933 B2 | 12/2003 | Asano |
| 6,662,041 B2 | 12/2003 | Burbank et al. |
| 6,699,205 B2 | 3/2004 | Fulton, III et al. |
| 6,712,774 B2 | 3/2004 | Voegele et al. |
| 6,712,836 B1 | 3/2004 | Berg et al. |
| 6,716,444 B1 | 4/2004 | Castro et al. |
| 6,725,083 B1 | 4/2004 | Burbank et al. |
| 6,730,042 B2 | 5/2004 | Fulton et al. |
| 6,730,044 B2 | 5/2004 | Stephens et al. |
| 6,746,661 B2 | 6/2004 | Kaplan |
| 6,746,773 B2 | 6/2004 | Llanos et al. |
| 6,752,154 B2 | 6/2004 | Fogarty et al. |
| 6,766,186 B1 | 7/2004 | Hoyns et al. |
| 6,774,278 B1 | 8/2004 | Ragheb et al. |
| 6,780,179 B2 | 8/2004 | Lee et al. |
| 6,824,507 B2 | 11/2004 | Miller |
| 6,824,527 B2 | 11/2004 | Gollobin |
| 6,846,320 B2 | 1/2005 | Ashby et al. |
| 6,862,470 B2 | 3/2005 | Burbank et al. |
| 6,863,685 B2 | 3/2005 | Davila et al. |
| 6,881,226 B2 | 4/2005 | Corbitt, Jr. et al. |
| 6,889,833 B2 | 5/2005 | Seiler et al. |
| 6,899,731 B2 | 5/2005 | Li et al. |
| 6,918,927 B2 | 7/2005 | Bates et al. |
| 6,936,014 B2 | 8/2005 | Vetter et al. |
| 6,939,318 B2 | 9/2005 | Stenzel |
| 6,945,973 B2 | 9/2005 | Bray |
| 6,951,564 B2 | 10/2005 | Espositio et al. |
| 6,958,044 B2 | 10/2005 | Burbank et al. |
| 6,992,233 B2 | 1/2006 | Drake et al. |
| 6,993,375 B2 | 1/2006 | Burbank et al. |
| 6,994,712 B1 | 2/2006 | Fisher et al. |
| 6,996,433 B2 | 2/2006 | Burbank et al. |
| 7,001,341 B2 | 2/2006 | Gellman et al. |
| 7,008,382 B2 | 3/2006 | Adams et al. |
| 7,014,610 B2 | 3/2006 | Koulik |
| 7,025,765 B2 | 4/2006 | Balbierz et al. |
| 7,041,047 B2 | 5/2006 | Gellman et al. |
| 7,044,957 B2 | 5/2006 | Foerster et al. |
| 7,047,063 B2 | 5/2006 | Burbank et al. |
| 7,083,576 B2 | 8/2006 | Zarins et al. |
| 7,125,397 B2 | 10/2006 | Woehr et al. |
| 7,135,978 B2 | 11/2006 | Gisselberg et al. |
| 7,160,258 B2 | 1/2007 | Imran et al. |
| 7,172,549 B2 | 2/2007 | Slater et al. |
| 7,189,206 B2 | 3/2007 | Quick et al. |
| 7,214,211 B2 | 5/2007 | Woehr et al. |
| 7,229,417 B2 | 6/2007 | Foerster et al. |
| 7,236,816 B2 | 6/2007 | Kumar et al. |
| 7,264,613 B2 | 9/2007 | Woehr et al. |
| 7,280,865 B2 | 10/2007 | Adler |
| 7,294,118 B2 | 11/2007 | Saulenas et al. |
| 7,297,725 B2 | 11/2007 | Winterton et al. |
| 7,329,402 B2 | 2/2008 | Unger et al. |
| 7,329,414 B2 | 2/2008 | Fisher et al. |
| 7,407,054 B2 | 8/2008 | Seiler et al. |
| 7,416,533 B2 | 8/2008 | Gellman et al. |
| 7,424,320 B2 | 9/2008 | Chesbrough et al. |
| 7,449,000 B2 | 11/2008 | Adams et al. |
| 7,527,610 B2 | 5/2009 | Erickson |
| 7,534,452 B2 | 5/2009 | Chernomorsky et al. |
| 7,535,363 B2 | 5/2009 | Gisselberg et al. |
| 7,565,191 B2 | 7/2009 | Burbank et al. |
| 7,569,065 B2 | 8/2009 | Chesbrough et al. |
| 7,577,473 B2 | 8/2009 | Davis et al. |
| 7,637,948 B2 | 12/2009 | Corbitt, Jr. |
| 7,651,505 B2 | 1/2010 | Lubock et al. |
| 7,668,582 B2 | 2/2010 | Sirimanne et al. |
| 7,670,350 B2 | 3/2010 | Sells |
| 7,783,336 B2 | 8/2010 | Macfarlane et al. |
| 7,792,569 B2 | 9/2010 | Burbank et al. |
| 7,819,819 B2 | 10/2010 | Quick et al. |
| 7,819,820 B2 | 10/2010 | Field et al. |
| 7,844,319 B2 | 11/2010 | Susil et al. |
| 7,871,438 B2 | 1/2011 | Corbitt, Jr. |
| 7,877,133 B2 | 1/2011 | Burbank et al. |
| 7,914,553 B2 | 3/2011 | Ferree |
| 7,945,307 B2 | 5/2011 | Lubock et al. |
| 7,978,825 B2 | 7/2011 | Ngo |
| 7,983,734 B2 | 7/2011 | Jones et al. |
| 8,011,508 B2 | 9/2011 | Seiler et al. |
| 8,027,712 B2 | 9/2011 | Sioshansi et al. |
| 8,052,658 B2 | 11/2011 | Field |
| 8,052,708 B2 | 11/2011 | Chesbrough et al. |
| 8,064,987 B2 | 11/2011 | Carr, Jr. |
| 8,128,641 B2 | 3/2012 | Wardle |
| 8,157,862 B2 | 4/2012 | Corbitt, Jr. |
| 8,306,602 B2 | 11/2012 | Sirimanne et al. |
| 8,311,610 B2 | 11/2012 | Ranpura |
| 8,320,993 B2 | 11/2012 | Sirimanne et al. |
| 8,320,994 B2 | 11/2012 | Sirimanne et al. |
| 8,320,995 B2 | 11/2012 | Schwamb, Jr. |
| 8,334,424 B2 | 12/2012 | Szypka |
| 8,361,082 B2 | 1/2013 | Jones et al. |
| 8,401,622 B2 | 3/2013 | Talpade et al. |
| 8,437,834 B2 | 5/2013 | Carr, Jr. |
| 8,442,623 B2 | 5/2013 | Nicoson et al. |
| 8,454,629 B2 | 6/2013 | Selis |
| 8,486,028 B2 | 7/2013 | Field |
| 8,579,931 B2 | 11/2013 | Chesbrough et al. |
| 8,626,269 B2 | 1/2014 | Jones et al. |
| 8,626,270 B2 | 1/2014 | Burbank et al. |
| 8,639,315 B2 | 1/2014 | Burbank et al. |
| 8,668,737 B2 | 3/2014 | Corbitt, Jr. |
| 8,680,498 B2 | 3/2014 | Corbitt et al. |
| 9,237,937 B2 | 1/2016 | Burbank et al. |
| 2001/0006616 A1 | 7/2001 | Leavitt et al. |
| 2002/0004060 A1 | 1/2002 | Heublein et al. |
| 2002/0016625 A1 | 2/2002 | Falotico et al. |
| 2002/0022883 A1 | 2/2002 | Burg |
| 2002/0026201 A1 | 2/2002 | Foerster et al. |
| 2002/0035324 A1 | 3/2002 | Sirimanne et al. |
| 2002/0044969 A1 | 4/2002 | Harden et al. |
| 2002/0045842 A1 | 4/2002 | Van Bladel et al. |
| 2002/0052572 A1 | 5/2002 | Franco et al. |
| 2002/0055731 A1 | 5/2002 | Atala et al. |
| 2002/0058868 A1 | 5/2002 | Hoshino et al. |
| 2002/0058882 A1 | 5/2002 | Fulton, III et al. |
| 2002/0077687 A1 | 6/2002 | Ahn |
| 2002/0082517 A1 | 6/2002 | Klein |

(56) References Cited

U.S. PATENT DOCUMENTS

| | | |
|---|---|---|
| 2002/0082519 A1 | 6/2002 | Miller et al. |
| 2002/0082682 A1 | 6/2002 | Barclay et al. |
| 2002/0082683 A1 | 6/2002 | Stinson et al. |
| 2002/0095204 A1 | 7/2002 | Thompson et al. |
| 2002/0095205 A1 | 7/2002 | Edwin et al. |
| 2002/0107437 A1 | 8/2002 | Sirimanne et al. |
| 2002/0133148 A1 | 9/2002 | Daniel et al. |
| 2002/0143359 A1 | 10/2002 | Fulton, III et al. |
| 2002/0165608 A1 | 11/2002 | Llanos et al. |
| 2002/0177776 A1 | 11/2002 | Crawford Kellar et al. |
| 2002/0193815 A1 | 12/2002 | Foerster et al. |
| 2002/0193867 A1 | 12/2002 | Gladdish, Jr. et al. |
| 2003/0032969 A1 | 2/2003 | Gannoe et al. |
| 2003/0036803 A1 | 2/2003 | McGhan |
| 2003/0051735 A1 | 3/2003 | Pavcnik et al. |
| 2003/0116806 A1 | 6/2003 | Kato |
| 2003/0165478 A1 | 9/2003 | Sokoll |
| 2003/0191355 A1 | 10/2003 | Ferguson |
| 2003/0199887 A1 | 10/2003 | Ferrera et al. |
| 2003/0225420 A1 | 12/2003 | Wardle |
| 2003/0233101 A1 | 12/2003 | Lubock et al. |
| 2003/0236573 A1 | 12/2003 | Evans et al. |
| 2004/0001841 A1 | 1/2004 | Nagavarapu et al. |
| 2004/0002650 A1 | 1/2004 | Mandrusov et al. |
| 2004/0016195 A1 | 1/2004 | Archuleta |
| 2004/0024304 A1 | 2/2004 | Foerster et al. |
| 2004/0059341 A1 | 3/2004 | Gellman et al. |
| 2004/0068312 A1 | 4/2004 | Sigg et al. |
| 2004/0073107 A1 | 4/2004 | Sioshansi et al. |
| 2004/0073284 A1 | 4/2004 | Bates et al. |
| 2004/0097981 A1 | 5/2004 | Selis |
| 2004/0101479 A1 | 5/2004 | Burbank et al. |
| 2004/0101548 A1 | 5/2004 | Pendharkar |
| 2004/0106891 A1 | 6/2004 | Langan et al. |
| 2004/0116802 A1 | 6/2004 | Jessop et al. |
| 2004/0124105 A1 | 7/2004 | Seiler et al. |
| 2004/0127765 A1 | 7/2004 | Seiler et al. |
| 2004/0133124 A1 | 7/2004 | Bates et al. |
| 2004/0153074 A1 | 8/2004 | Bojarski et al. |
| 2004/0162574 A1 | 8/2004 | Viola |
| 2004/0167619 A1 | 8/2004 | Case et al. |
| 2004/0204660 A1 | 10/2004 | Fulton et al. |
| 2004/0210208 A1 | 10/2004 | Paul et al. |
| 2004/0213756 A1 | 10/2004 | Michal et al. |
| 2004/0236212 A1 | 11/2004 | Jones et al. |
| 2004/0236213 A1 | 11/2004 | Jones et al. |
| 2004/0253185 A1 | 12/2004 | Herweck et al. |
| 2004/0265371 A1 | 12/2004 | Looney et al. |
| 2005/0020916 A1 | 1/2005 | MacFarlane et al. |
| 2005/0033157 A1 | 2/2005 | Klien et al. |
| 2005/0033195 A1 | 2/2005 | Fulton et al. |
| 2005/0036946 A1 | 2/2005 | Pathak et al. |
| 2005/0038355 A1 | 2/2005 | Gellman et al. |
| 2005/0045192 A1 | 3/2005 | Fulton et al. |
| 2005/0059887 A1 | 3/2005 | Mostafavi et al. |
| 2005/0059888 A1 | 3/2005 | Sirimanne et al. |
| 2005/0065354 A1 | 3/2005 | Roberts |
| 2005/0065453 A1 | 3/2005 | Shabaz et al. |
| 2005/0080337 A1 | 4/2005 | Sirimanne et al. |
| 2005/0080339 A1 | 4/2005 | Sirimanne et al. |
| 2005/0085724 A1 | 4/2005 | Sirimanne et al. |
| 2005/0100580 A1 | 5/2005 | Osborne et al. |
| 2005/0112151 A1 | 5/2005 | Horng |
| 2005/0113659 A1 | 5/2005 | Pothier et al. |
| 2005/0119562 A1 | 6/2005 | Jones et al. |
| 2005/0142161 A1 | 6/2005 | Freeman et al. |
| 2005/0143650 A1 | 6/2005 | Winkel |
| 2005/0165305 A1 | 7/2005 | Foerster et al. |
| 2005/0175657 A1 | 8/2005 | Hunter et al. |
| 2005/0181007 A1 | 8/2005 | Hunter et al. |
| 2005/0208122 A1 | 9/2005 | Allen et al. |
| 2005/0216018 A1 | 9/2005 | Sennett |
| 2005/0234336 A1 | 10/2005 | Beckman et al. |
| 2005/0268922 A1 | 12/2005 | Conrad et al. |
| 2005/0273002 A1 | 12/2005 | Goosen et al. |
| 2005/0277871 A1 | 12/2005 | Selis |
| 2006/0004440 A1 | 1/2006 | Stinson |
| 2006/0009800 A1 | 1/2006 | Christianson et al. |
| 2006/0025677 A1 | 2/2006 | Verard et al. |
| 2006/0025795 A1 | 2/2006 | Chesbrough et al. |
| 2006/0036158 A1 | 2/2006 | Field et al. |
| 2006/0036159 A1 | 2/2006 | Sirimanne et al. |
| 2006/0074443 A1 | 4/2006 | Foerster et al. |
| 2006/0079770 A1 | 4/2006 | Sirimanne et al. |
| 2006/0079805 A1 | 4/2006 | Miller et al. |
| 2006/0079829 A1 | 4/2006 | Fulton et al. |
| 2006/0079888 A1 | 4/2006 | Mulier et al. |
| 2006/0116573 A1 | 6/2006 | Field et al. |
| 2006/0122503 A1 | 6/2006 | Burbank et al. |
| 2006/0155190 A1 | 7/2006 | Burbank et al. |
| 2006/0173280 A1 | 8/2006 | Goosen et al. |
| 2006/0173296 A1 | 8/2006 | Miller et al. |
| 2006/0177379 A1 | 8/2006 | Asgari |
| 2006/0217635 A1 | 9/2006 | McCombs et al. |
| 2006/0235298 A1 | 10/2006 | Kotmel et al. |
| 2006/0241385 A1 | 10/2006 | Dietz |
| 2006/0241411 A1* | 10/2006 | Field ...................... A61B 19/54 600/431 |
| 2006/0292690 A1 | 12/2006 | Liu et al. |
| 2007/0021642 A1 | 1/2007 | Lamoureux et al. |
| 2007/0038145 A1 | 2/2007 | Field |
| 2007/0057794 A1 | 3/2007 | Gisselberg et al. |
| 2007/0083132 A1 | 4/2007 | Sharrow |
| 2007/0087026 A1 | 4/2007 | Field |
| 2007/0106152 A1 | 5/2007 | Kantrowitz et al. |
| 2007/0135711 A1 | 6/2007 | Chernomorsky et al. |
| 2007/0142725 A1 | 6/2007 | Hardin et al. |
| 2007/0167736 A1 | 7/2007 | Dietz et al. |
| 2007/0167749 A1 | 7/2007 | Yarnall et al. |
| 2007/0239118 A1 | 10/2007 | Ono et al. |
| 2007/0276492 A1 | 11/2007 | Andrews et al. |
| 2007/0287933 A1 | 12/2007 | Phan et al. |
| 2008/0033280 A1 | 2/2008 | Lubock et al. |
| 2008/0039819 A1 | 2/2008 | Jones et al. |
| 2008/0058640 A1 | 3/2008 | Jones et al. |
| 2008/0091120 A1 | 4/2008 | Fisher |
| 2008/0097199 A1 | 4/2008 | Mullen |
| 2008/0121242 A1 | 5/2008 | Revie et al. |
| 2008/0188768 A1 | 8/2008 | Zarins et al. |
| 2008/0249436 A1 | 10/2008 | Darr |
| 2008/0269638 A1 | 10/2008 | Cooke et al. |
| 2008/0294039 A1 | 11/2008 | Jones et al. |
| 2009/0000629 A1 | 1/2009 | Hornscheidt et al. |
| 2009/0024225 A1 | 1/2009 | Stubbs |
| 2009/0030309 A1 | 1/2009 | Jones et al. |
| 2009/0069713 A1 | 3/2009 | Adams et al. |
| 2009/0076484 A1 | 3/2009 | Fukaya |
| 2009/0093714 A1 | 4/2009 | Chesbrough et al. |
| 2009/0131825 A1 | 5/2009 | Burbank et al. |
| 2009/0171198 A1 | 7/2009 | Jones et al. |
| 2009/0216118 A1 | 8/2009 | Jones et al. |
| 2009/0287078 A1 | 11/2009 | Burbank et al. |
| 2010/0010341 A1 | 1/2010 | Talpade et al. |
| 2010/0010342 A1 | 1/2010 | Burbank et al. |
| 2010/0030072 A1 | 2/2010 | Casanova et al. |
| 2010/0030149 A1 | 2/2010 | Carr, Jr. |
| 2010/0042041 A1 | 2/2010 | Tune et al. |
| 2010/0082102 A1 | 4/2010 | Govil et al. |
| 2010/0094169 A1 | 4/2010 | Lubock et al. |
| 2010/0198059 A1 | 8/2010 | Burbank et al. |
| 2010/0204570 A1 | 8/2010 | Lubock |
| 2010/0298696 A1 | 11/2010 | Field et al. |
| 2010/0298698 A1 | 11/2010 | Burbank et al. |
| 2010/0324416 A1 | 12/2010 | Burbank et al. |
| 2010/0331668 A1 | 12/2010 | Ranpura |
| 2011/0092815 A1 | 4/2011 | Burbank et al. |
| 2011/0184280 A1 | 7/2011 | Jones et al. |
| 2011/0184449 A1 | 7/2011 | Lubock et al. |
| 2012/0078092 A1 | 3/2012 | Jones et al. |
| 2012/0116215 A1 | 5/2012 | Jones et al. |
| 2012/0215230 A1 | 8/2012 | Lubock et al. |
| 2012/0277859 A1 | 11/2012 | Govil et al. |
| 2013/0144157 A1 | 6/2013 | Jones et al. |
| 2013/0184562 A1 | 7/2013 | Talpade et al. |

(56) References Cited

U.S. PATENT DOCUMENTS

| | | |
|---|---|---|
| 2013/0190616 A1 | 7/2013 | Casanova et al. |
| 2013/0281847 A1 | 10/2013 | Jones et al. |
| 2013/0310686 A1 | 11/2013 | Jones et al. |
| 2014/0058258 A1 | 2/2014 | Chesbrough et al. |
| 2014/0094698 A1 | 4/2014 | Burbank et al. |
| 2014/0114186 A1 | 4/2014 | Burbank et al. |
| 2014/0142696 A1 | 5/2014 | Corbitt, Jr. |
| 2014/0239528 A1 | 8/2014 | Govil et al. |
| 2014/0243675 A1 | 8/2014 | Burbank et al. |
| 2015/0051477 A1 | 2/2015 | Jones et al. |
| 2015/0164610 A1 | 6/2015 | Field et al. |
| 2015/0245883 A1 | 9/2015 | Talpade et al. |
| 2016/0015475 A1 | 1/2016 | Jones et al. |
| 2016/0120510 A1 | 5/2016 | Burbank et al. |
| 2016/0128797 A1 | 5/2016 | Burbank et al. |
| 2016/0199150 A1 | 7/2016 | Field et al. |
| 2017/0042664 A1 | 2/2017 | Corbitt, Jr. |
| 2017/0100203 A1 | 4/2017 | Field et al. |
| 2017/0119492 A1 | 5/2017 | Chesbrough et al. |
| 2017/0128154 A1 | 5/2017 | Casanova et al. |

FOREIGN PATENT DOCUMENTS

| | | |
|---|---|---|
| EP | 0255123 A2 | 2/1988 |
| EP | 0292936 A2 | 11/1988 |
| EP | 0458745 A1 | 11/1991 |
| EP | 0475077 A2 | 3/1992 |
| EP | 0552924 A1 | 7/1993 |
| EP | 0769281 A2 | 4/1997 |
| EP | 1114618 A2 | 7/2001 |
| EP | 1163888 A1 | 12/2001 |
| EP | 1281416 A2 | 6/2002 |
| EP | 1364628 A1 | 11/2003 |
| EP | 1493451 A1 | 1/2005 |
| EP | 1767167 A2 | 3/2007 |
| FR | 2646674 A3 | 11/1990 |
| FR | 2853521 A1 | 10/2004 |
| GB | 708148 | 4/1954 |
| JP | 2131757 A | 5/1990 |
| JP | 2006516468 A | 7/2006 |
| JP | 2007537017 A | 12/2007 |
| WO | 8906978 A1 | 8/1989 |
| WO | 9112823 A1 | 9/1991 |
| WO | 9314712 A1 | 8/1993 |
| WO | 9317671 A1 | 9/1993 |
| WO | 9317718 A1 | 9/1993 |
| WO | 9416647 A1 | 8/1994 |
| WO | 9507057 A1 | 3/1995 |
| WO | 9806346 A1 | 2/1998 |
| WO | 9908607 A1 | 2/1999 |
| WO | 9935966 A1 | 7/1999 |
| WO | 9951143 A1 | 10/1999 |
| WO | 0023124 A1 | 4/2000 |
| WO | 0024332 A1 | 5/2000 |
| WO | 0028554 A1 | 5/2000 |
| WO | 0054689 A1 | 9/2000 |
| WO | 0108578 A1 | 2/2001 |
| WO | 0170114 A1 | 9/2001 |
| WO | 0207786 A2 | 1/2002 |
| WO | 0241786 A2 | 5/2002 |
| WO | 03000308 A1 | 1/2003 |
| WO | 2004045444 A2 | 6/2004 |
| WO | 2005013832 A1 | 2/2005 |
| WO | 2005089664 A1 | 9/2005 |
| WO | 2005112787 A2 | 12/2005 |
| WO | 2006012630 A2 | 2/2006 |
| WO | 2006056739 A2 | 6/2006 |
| WO | 2006097331 A2 | 9/2006 |
| WO | 2006105353 A2 | 10/2006 |
| WO | 2007067255 A1 | 6/2007 |
| WO | 2007069105 A2 | 6/2007 |
| WO | 2008077081 A2 | 6/2008 |

OTHER PUBLICATIONS

Fucci, V., et al., "Large Bowel Transit Times Using Radioopaque Markers in Normal Cats", J. of Am. Animal Hospital Assn., Nov.-Dec. 1995 31 (6) 473-477.

Schindlbeck, N.E., et al., "Measurement of Colon Transit Time", J. of Gastroenterology, No. 28, pp. 399-404, 1990.

Shiga, et al., Preparation of Poly(D, L-lactide) and Copoly(lactide-glycolide) Microspheres of Uniform Size, J. Pharm. Pharmacol. 1996 48:891-895.

Eiselt, P. et al, "Development of Technologies Aiding Large—Tissue Engineering", Biotechnol. Prog., vol. 14, No. 1, pp. 134-140, 1998.

Crook, et al. (Prostate Motion During Standard Radiotherapy As Assessed by Fiducial Markers, 1995, Radiotherapy and Oncology 37:35-42.)

Shah, et al. (Polyethylene Glycol as a Binder for Tablets, vol. 66, No. 11, Nov. 1977, Journal of Pharmaceutical Sciences).

Fajardo, Laurie, et al., "Placement of Endovascular Embolization Microcoils to Localize the Site of Breast Lesions Removed at Stereotactic Core Biopsy", Radiology, Jan. 1998, pp. 275-278, vol. 206—No. 1.

H. J. Gent, M.D., et al., Stereotaxic Needle Localization and Cytological Diagnosis of Occult Breast Lesions, Annals of Surgery, Nov. 1986, pp. 580-584, vol. 204—No. 5.

Meuris, Bart, "Calcification of Aortic Wall Tissue in Prosthetic Heart Valves: Initiation, Influencing Factors and Strategies Towards Prevention", Thesis, 2007, pp. 21-36, Leuven University Press; Leuven, Belgium.

Jong-Won Rhie, et al. "Implantation of Cultured Preadipocyte Using Chitosan/Alginate Sponge", Key Engineering Materials, Jul. 1, 2007, pp. 346-352, XP008159356, ISSN: 0252-1059, DOI: 10.4028/www.scientific.net/KEM.342-343.349, Department of Plastic Surgery, College of Medicine, The Catholic University of Korea, Seoul Korea.

Press release for Biopsys Ethicon Endo-Surgery (Europe) GmbH; The Mammotome Vacuum Biopsy System. From: http://www.medicine-news.com/articles/devices/mammotome.html. 3 pages.

Johnson & Johnson: Breast Biopsy (minimally invasive): Surgical Technique: Steps in the MAMOTOME Surgical Procedure. From http://www.jnjgateway.com. 3 pages.

Johnson & Johnson: New Minimally Invasive Breast Biopsy Device Receives Marketing Clearance in Canada; Aug. 6, 1999. From http://www.jnjgateway.com. 4 pages.

Johnson & Johnson: Mammotome Hand Held Receives FDA Marketing Clearance for Minimally Invasive Breast Biopises; Sep. 1, 1999. From From http://www.jnjgateway.com. 5 pages.

Johnson & Johnson: The Mammotome Breast Biopsy System. From: http://www.breastcareinfo.com/aboutm.htm. 6 pages.

Cook Incorporated: Emoblization and Occlusion. From: www.cookgroup.com 6 pages.

Liberman, Laura, et al. Percutaneous Removal of Malignant Mammographic Lesions at Stereotactic Vacuum-assisted Biopsy. From: The Departments of Radiology, Pathology, and Surgery. Memorial Sloan-Kettering Cancer Center. From the 1997 RSNA scientific assembly. vol. 206, No. 3. pp. 711-715.

\* cited by examiner

MARKER DELIVERY DEVICE FOR TISSUE MARKER PLACEMENT

This application is a continuation of U.S. patent application Ser. No. 12/595,010, filed Oct. 7, 2009, now U.S. Pat. No. 8,670,818, which is a U.S. national phase of International Application No. PCT/US2008/088558, filed Dec. 30, 2008.

BACKGROUND OF THE INVENTION

1. Field of the Invention

The present invention relates to medical devices, and, more particularly, to a marker delivery device for percutaneous tissue marker placement.

2. Description of the Related Art

Tissue biopsies are commonly performed on many areas and organs of the human body where it is desirable to ascertain whether or not a lesion or other tissue to be biopsied is cancerous. Often, the lesion or other tissue to be biopsied is identified through use of an imaging technique, such as a computerized axial tomography (CAT) scan, ultrasonography, and mammography.

In breast biopsies, for example, the lesion typically is so small that the biopsy reduces its size to the extent that it is no longer visible by the imaging method employed. In such circumstances, it is desirable to place a tissue marker at the site of the biopsy to enable the medical practitioner subsequently to locate the lesion quickly and accurately in the event complete removal of the affected tissue is indicated. The tissue marker is placed at the biopsy site, for example, by a marker delivery device having a needle cannula that houses the tissue marker.

In some marker delivery devices, the marker may not be completely ejected from the cannula, or may be drawn back into or toward the cannula by the vacuum created upon the withdrawal of the cannula, which results in the marker being moved from the intended site, leading to inaccurate identification of the location of the biopsy area. Another issue is the safe disposal of the marker delivery device after use, particularly the safe disposal of the cannula portion of the marker delivery device that is inserted into the tissue of the patient, which typically has a sharp point.

SUMMARY OF THE INVENTION

The invention provides, according to one aspect thereof, a marker delivery device configured to fully deliver the tissue marker at a delivery site in the patient where the tissue marker is less likely to migrate, which is achieved by delivering the tissue marker via a rigid cannula having a flexible portion for directing the distal end of the cannula, for example, into tissue adjacent a biopsy site. The invention provides, according to another aspect thereof, a marker delivery device configured to facilitate the safe disposal of the marker delivery device after use. The marker delivery device may be used, for example, in association with various imaging systems, such as X-ray, ultrasound, MRI etc.

The invention, in one form thereof, is directed to a marker delivery device configured for deploying a tissue marker. The marker delivery device includes a handle having a chamber. A cannula is configured for holding the tissue marker for deployment. The cannula has a side wall surrounding a lumen that extends along a lengthwise extent of the cannula. The cannula has a flexible portion formed by a slot arrangement having of a plurality of peripheral slots extending through the side wall of the cannula to the lumen. The plurality of peripheral slots is spaced apart to be substantially parallel along the lengthwise extent of the cannula to facilitate a flexure at the flexible portion of the cannula. A marker introducer rod is movably disposed in the lumen of the cannula. The marker introducer rod has a flexible region that corresponds to the flexible portion of the cannula. A deployment mechanism is mounted to the handle and configured to displace the marker introducer rod for deploying the tissue marker upon an actuation of the deployment mechanism. A retraction mechanism is mounted to the handle and is configured to facilitate a complete retraction of both the cannula and the marker introducer rod into the chamber of the housing of the handle upon an actuation of the retraction mechanism.

The invention, in another form thereof, is directed to a marker delivery device configured for deploying a tissue marker. The marker delivery device includes a handle configured to be grasped by a user. A cannula has a proximal end and a distal end, the proximal end being coupled to the handle. The cannula is substantially rigid and has a side wall surrounding a lumen that extends along a lengthwise extent of the cannula. The cannula has a flexible portion formed by a slot arrangement having of a plurality of peripheral slots extending through the side wall of the cannula to the lumen. The slots of the plurality of peripheral slots are spaced apart to be substantially parallel along the lengthwise extent of the cannula to facilitate a flexure at the flexible portion of the cannula. A marker introducer rod is movably disposed in the lumen of the cannula to effect a deployment of the tissue marker from the distal end of the cannula. The marker introducer rod has an actuation end and a marker deployment end, and a flexible region that corresponds to the flexible portion of the cannula.

The invention, in another form thereof, is directed to a marker delivery device configured for deploying a tissue marker. The marker delivery device includes a handle configured to be to be grasped by a user. The handle includes a housing having a front end and a back end, with a chamber located between the front end and the back end, and having a hole leading from the chamber to the exterior of the handle. A cannula has a proximal end, a distal end, and a lumen extending along a lengthwise extent of the cannula between the proximal end and the distal end. The cannula is positioned in the handle such that the cannula retractably extends through the hole beyond the front end of the housing. A marker introducer rod is movably disposed in the lumen of the cannula to effect a deployment of the tissue marker from the distal end of the cannula. The marker introducer rod has an actuation end and a marker deployment end. A deployment mechanism is mounted to the housing. The deployment mechanism is coupled to the actuation end of the marker introducer rod. The deployment mechanism is configured to displace the marker introducer rod for deploying the tissue marker upon an actuation of the deployment mechanism. A retraction mechanism is mounted to the housing, and is coupled to the proximal end of the cannula. The retraction mechanism is configured to facilitate a complete retraction of both the cannula and the marker introducer rod into the chamber of the housing of the handle upon an actuation of the retraction mechanism.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention, and such exemplifications are not to be construed as limiting the scope of the invention in any manner.

DETAILED DESCRIPTION OF THE INVENTION

Figure 1:
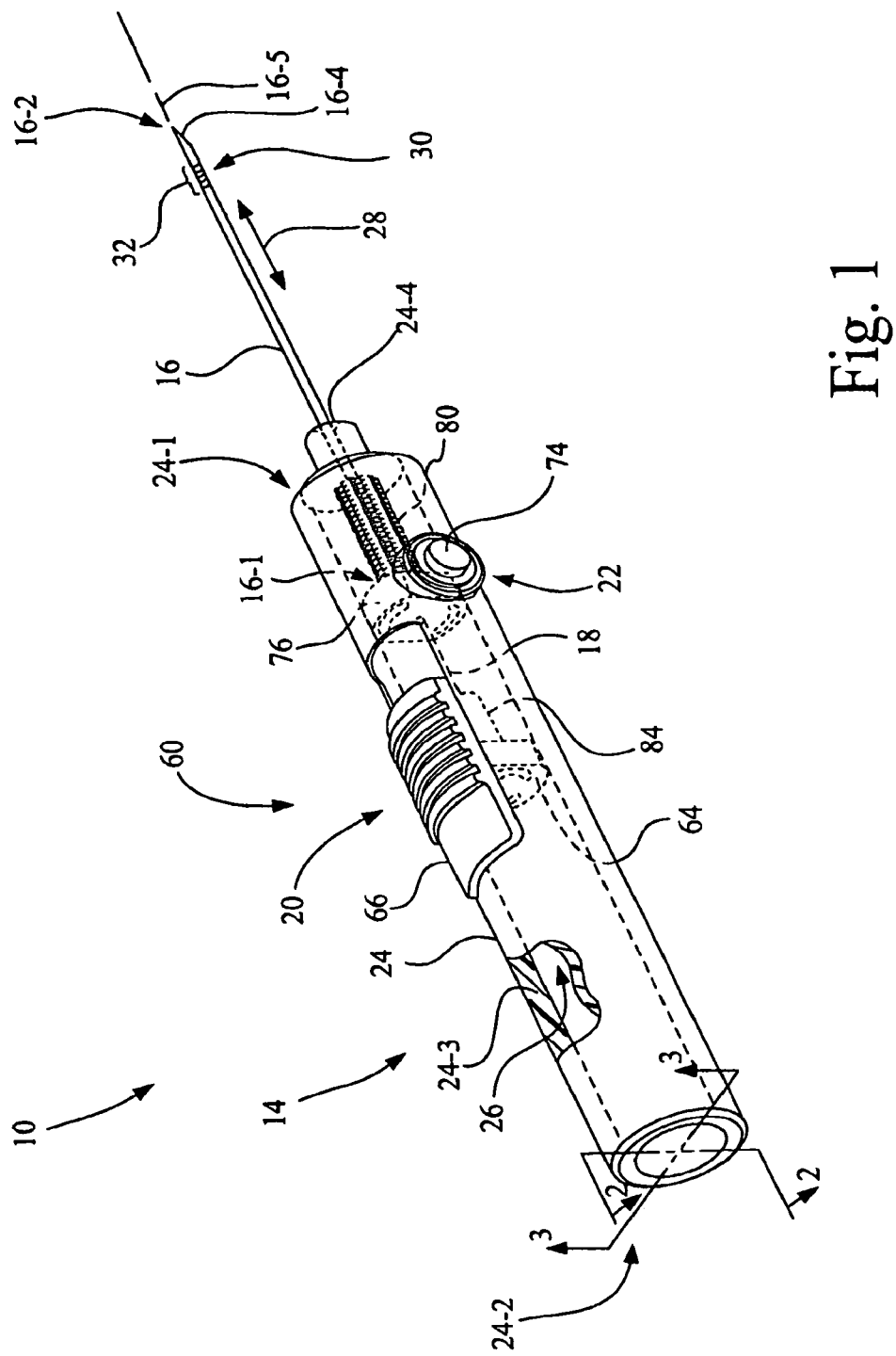
FIG. 1 is a perspective view of a marker delivery device configured for deploying a tissue marker in accordance with an embodiment of the present invention.
Figure 2:
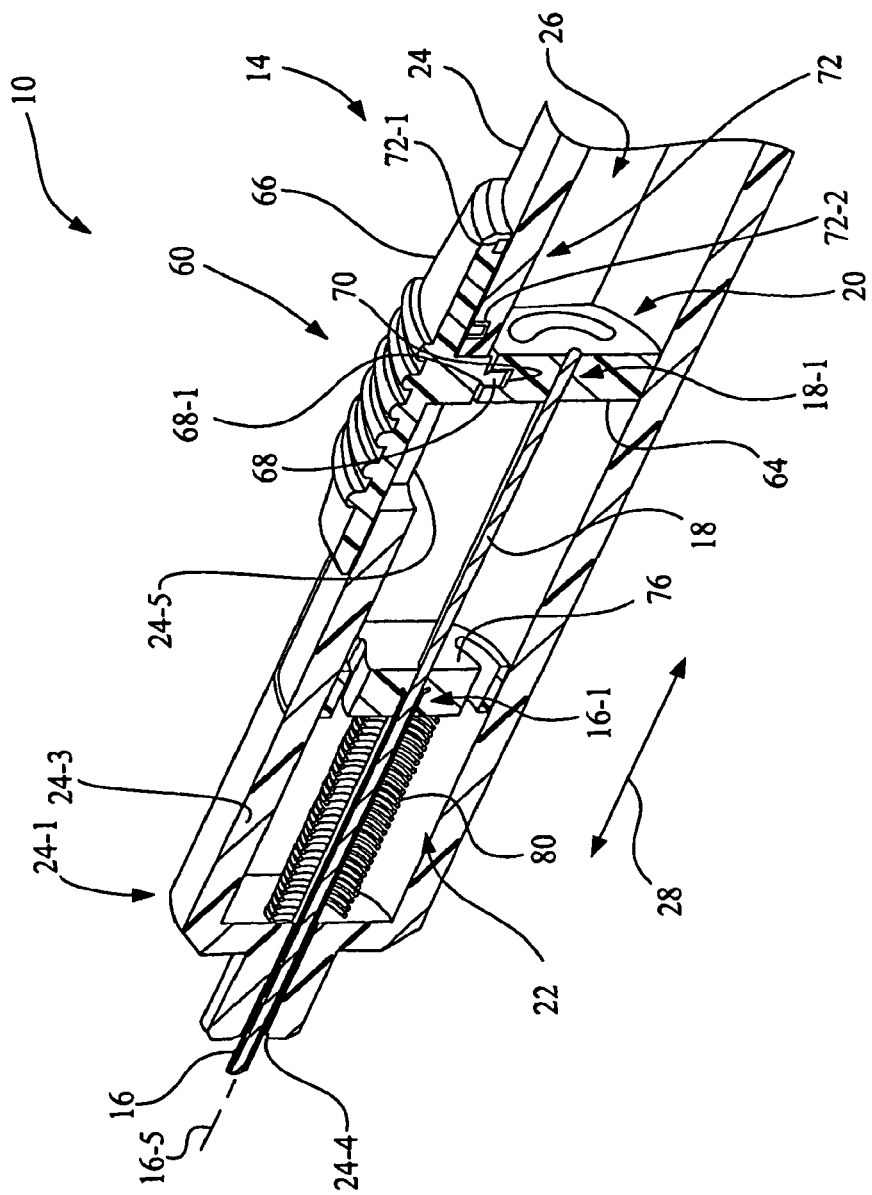
FIG. 2 is a section view of a portion of the marker delivery device of FIG. 1 taken along plane 2-2.
Figure 3:
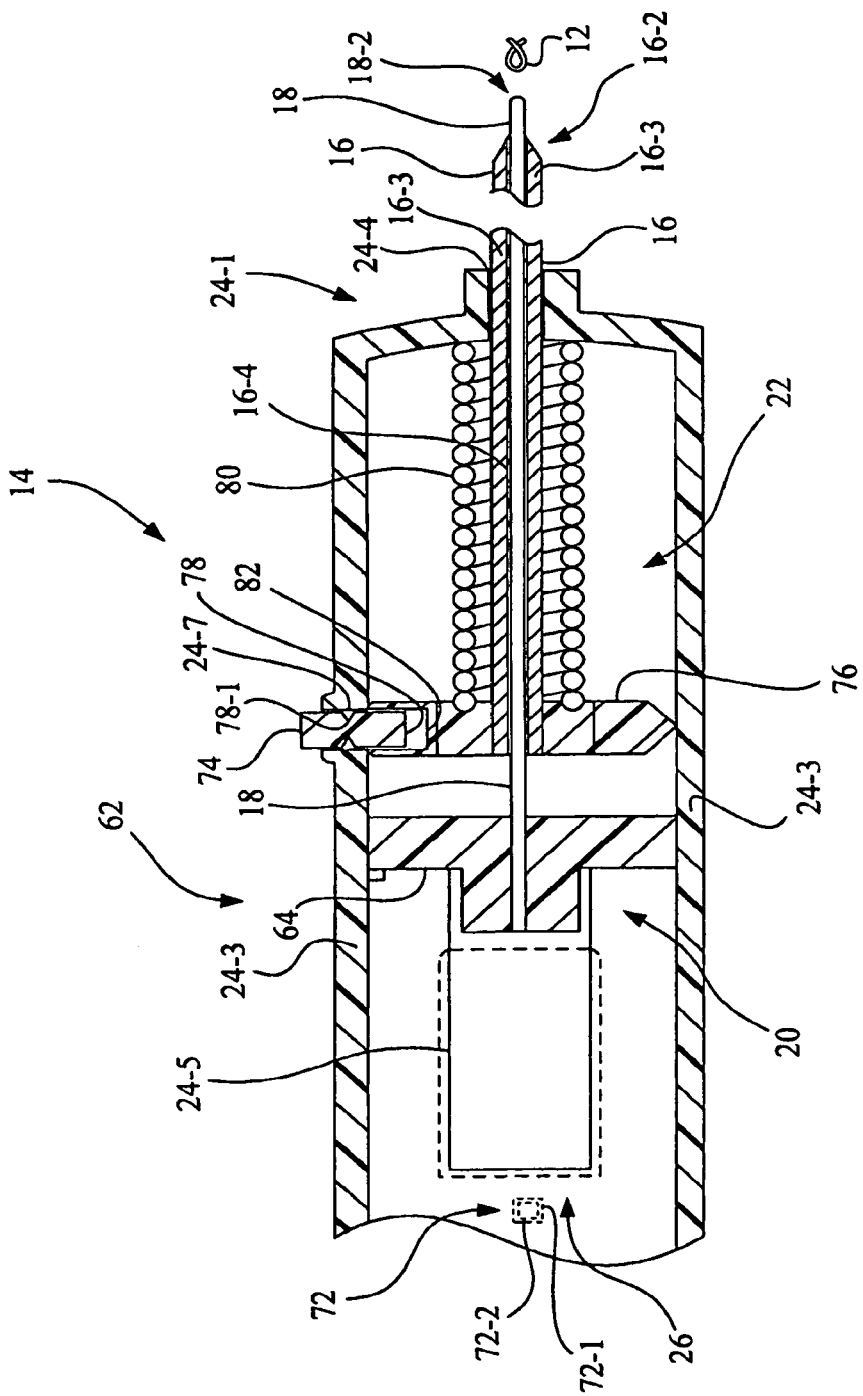
FIG. 3 is a section view of a portion of the marker delivery device of FIG. 1 taken along plane 3-3.

Referring now to the drawings, and more particularly to FIGS. 1-3, there is shown a marker delivery device 10 configured for deploying a tissue marker 12, in accordance with an embodiment of the present invention.

Marker delivery device 10 includes a handle 14, a cannula 16, a marker introducer rod 18, a deployment mechanism 20 and a retraction mechanism 22.

Handle 14 is configured to be grasped by a user, i.e., is of an appropriate size and shape to be grasped by the hand of the user of marker delivery device 10. Handle 14 includes a housing 24 having a front end 24-1, a back end 24-2 and a side wall 24-3, with a longitudinal chamber 26 located between front end 24-1 and back end 24-2 that is surrounded by side wall 24-3. A hole 24-4 leads from chamber 26 through front end 24-1 of housing 24 to the exterior of handle 14. A trigger slot 24-5 extends through side wall 24-3 of housing 24.

Cannula 16 is configured for holding tissue marker 12 for deployment into a tissue mass of a patient, and may be in the form of a hollow needle. Cannula 16 is positioned in handle 14 such that cannula 16 extends through the hole 24-4 beyond the front end 24-1 of housing 24 prior to marker deployment. Cannula 16 has a proximal end 16-1 and a distal end 16-2, with the proximal end 16-1 being coupled to handle 14. Cannula 16 has a side wall 16-3 that surrounds a lumen 16-4 that extends along a lengthwise extent 28 along a longitudinal axis 16-5 of cannula 16. Cannula 16 is substantially rigid, and may be made, for example, from a metallic material, such as for example, stainless steel, nitinol, a nickel-chromium alloy, titanium, etc.

Figure 4A:
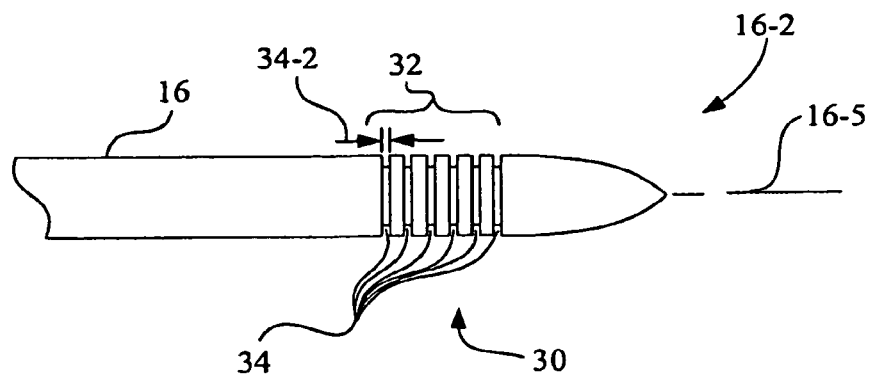
FIG. 4A is a top view of a portion of the cannula of the marker delivery device of FIG. 1 depicting a flexible portion of the cannula.
Figure 4B:
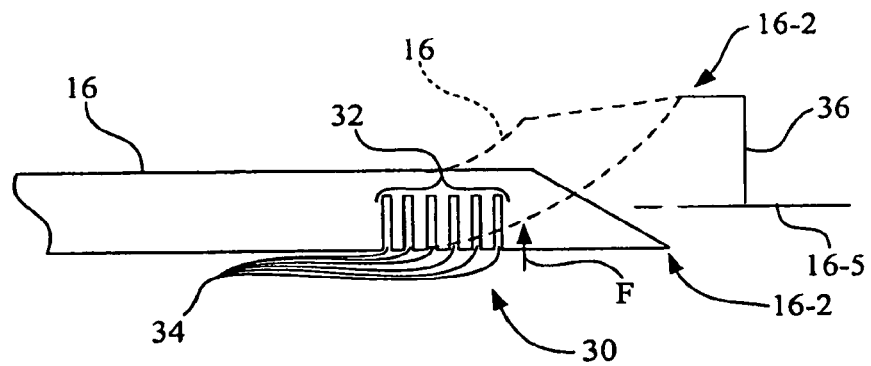
FIG. 4B is a side view of the flexible portion of the cannula of FIG. 4A, showing in phantom lines the flexure of the flexible portion of the cannula relative to non-flexure.
Figure 4C:
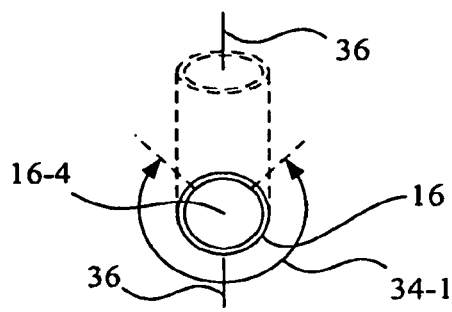
FIG. 4C is an end view of the cannula of FIG. 4A from the perspective of looking into the lumen of the cannula from the distal end of the cannula, also showing in phantom lines the flexure of the flexible portion of the cannula relative to non-flexure.

Referring also to FIGS. 4A-4C, cannula 16 has a flexible portion 30 formed by a slot arrangement 32 having of a plurality of peripheral slots 34 arranged circumferentially around cannula 16. Slot arrangement 32 may be formed in cannula 16, for example, by making cuts in cannula 16, such as through the use of a cutting laser. In the present embodiment, flexible portion 30 of cannula 16 is located closer to the distal end 16-2 of cannula 16 than to proximal end 16-1 of cannula 16. The plurality of peripheral slots 34 extends through the side wall 16-2 of cannula 16 to lumen 16-4. Also, as illustrated in FIG. 4C, in the present embodiment a circumferential extent 34-1 of each of the slots of the plurality of peripheral slots 34 of slot arrangement 32 is approximately two-thirds of the total circumference of cannula 16.

As illustrated in FIGS. 4A and 4B, in the present embodiment the plurality of peripheral slots 34 are spaced apart from one another to be substantially parallel along the lengthwise extent 28 of cannula 16 to facilitate a flexure at flexible portion 30 of cannula 16. FIG. 4B shows in phantom lines the flexure of the flexible portion 30 of cannula 16 relative to a non-flexure of cannula 16. As illustrated in FIGS. 4B and 4C, the configuration of the plurality of peripheral slots 34 (e.g., the circumferential placement of the slots along cannula 16) may be selected so that the flexure occurs along a single predetermined plane 36. In the present embodiment, for example, each of the substantially parallel plurality of peripheral slots 34 is arranged to be orthogonal to the longitudinal axis 16-5 of cannula 16.

The configuration of the plurality of peripheral slots 34 and the material forming cannula 16 may be selected such that the flexure does not result in a permanent deformation of cannula 16. For example, a slot width 34-2 relative to longitudinal axis 16-5 of the slots, the circumferential extent 34-1 of the slots, the axial placement of the slots along cannula 16, and the material used to form cannula 16 may be selected, through empirical studies and/or through materials analysis, so that flexible portion 30 formed by slot arrangement 32 will flex (e.g., bend at an acute angle with respect to longitudinal axis 16-5) when the distal end 16-2 of cannula 16 is acted on by an external force (F), and then return to the pre-deflected state, e.g., straight along longitudinal axis 16-5, when the external force (F) is removed.

Figure 5:
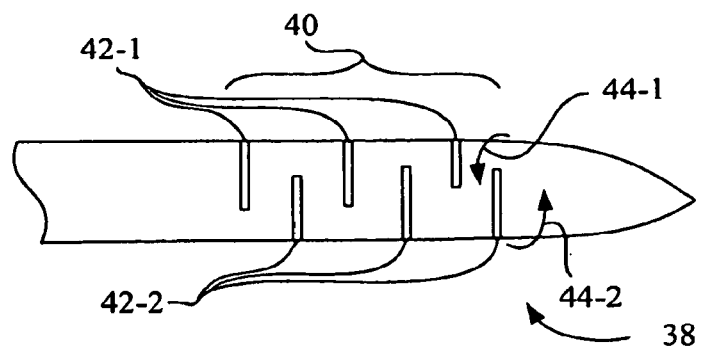
FIG. 5 is a top view of an alternative configuration of the flexible portion of the marker delivery device of FIG. 1.

FIG. 5 shows another slot arrangement 38 that may be used as an alternative to slot arrangement 32 shown in FIGS. 4A-4C. Slot arrangement 38 may be formed in cannula 16, for example, by making cuts in cannula 16, such as through the use of a cutting laser. Slot arrangement 38 includes of a plurality of peripheral slots 40 arranged circumferentially around cannula 16. The plurality of peripheral slots 40 include a first set of peripheral slots 42-1 having a first circumferential extent 44-1 and a second set of peripheral slots 42-2 having a second circumferential extent 44-2. The first circumferential extent 44-1 of the first set of peripheral slots 42-1 is circumferentially staggered with respect to the second circumferential extent 44-2 of the second set of peripheral slots 42-2.

Figure 6:
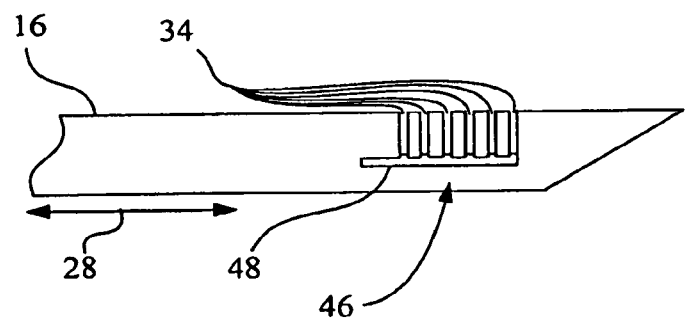
FIG. 6 is a top view of another alternative configuration of the flexible portion of the cannula of the marker delivery device of FIG. 1.

FIG. 6 shows another slot arrangement 46 that may be used as a further alternative to slot arrangement 32 shown in FIGS. 4A-4C, and includes the plurality of peripheral slots 34 arranged circumferentially around cannula 16, but in addition includes an axial slot 48 that extends along the lengthwise extent 28 of cannula 16 to link at least a portion, or all, of the plurality of peripheral slots 34 in a continuous slot arrangement. Slot arrangement 46 may be formed in cannula 16, for example, by making cuts in cannula 16, such as through the use of a cutting laser.

Figure 7:
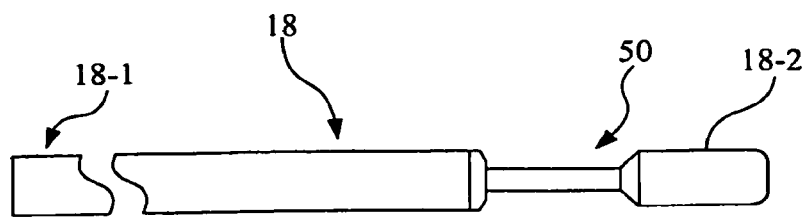
FIG. 7 is a side view of a portion of the marker introducer rod of the marker delivery device of FIG. 1, showing the actuation end, the marker deployment end, and the flexible region.

Referring again to FIGS. 2 and 3, marker introducer rod 18 is movably disposed in lumen 16-4 of cannula 16 to effect a deployment of tissue marker 12 from the distal end 16-2 of cannula 16. Referring also to FIG. 7, marker introducer rod 18 has an actuation end 18-1 and a marker deployment end 18-2, and has a flexible region 50 that corresponds to the flexible portion 30 of cannula 16. Accordingly, as flexible portion 30 of cannula 16 flexes, the flexible region 50 also flexes, while retaining the ability of marker introducer rod 18 to move longitudinally along lumen 16-4 to effect a deployment of tissue marker 12.

The flexible region 50 of marker introducer rod 18 may be formed as a flexible metallic element or a flexible plastic element, which in the present embodiment may be of reduced diameter with respect to a diameter of the remainder of marker introducer rod 18. Also, the remainder of marker introducer rod 18 may be formed from metal or plastic.

Figure 8:
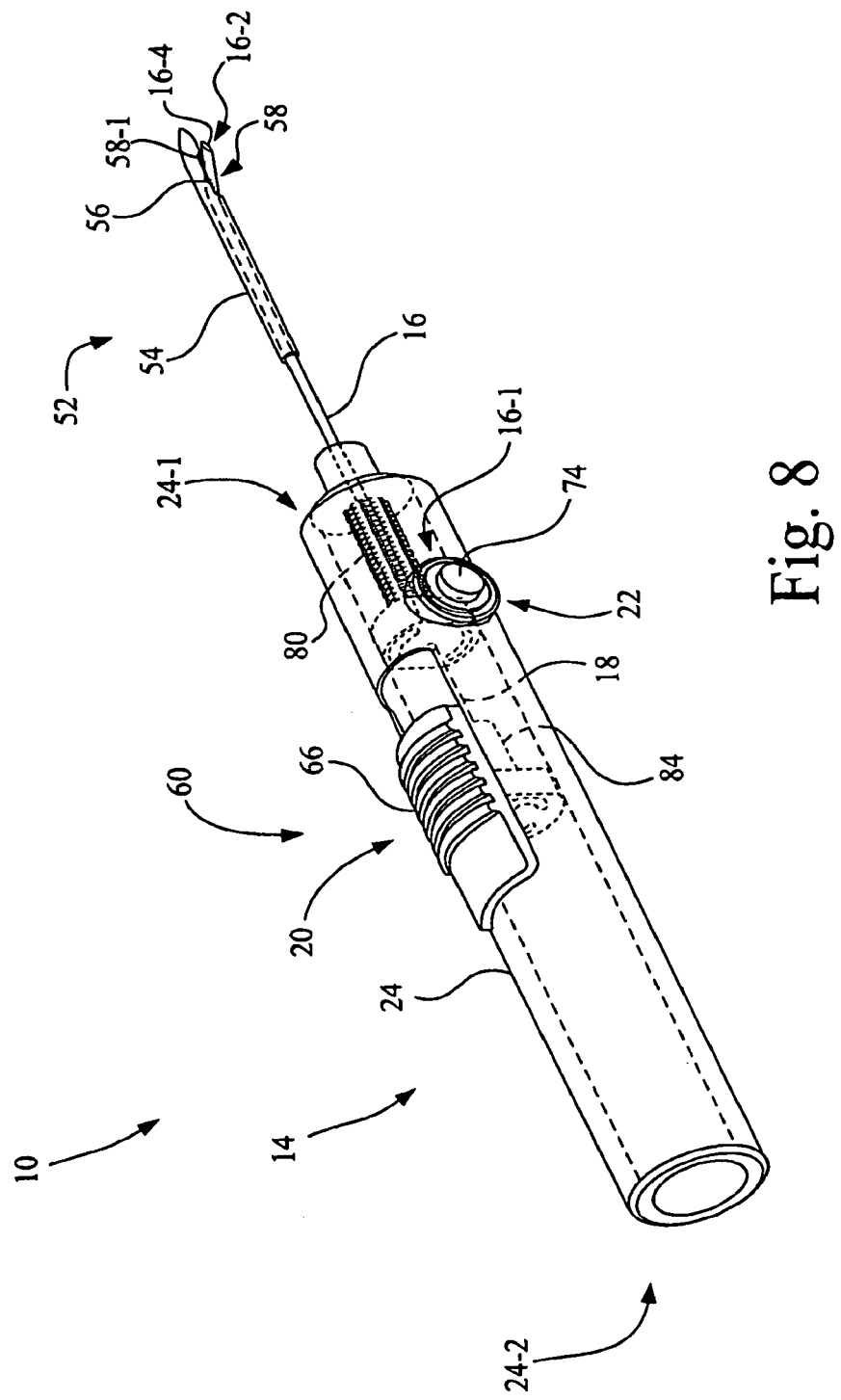
FIG. 8 is a perspective view of the marker delivery device of FIG. 1 used in conjunction with a biopsy device, showing a flexure of flexible portion of the cannula.

FIG. 8 illustrates an exemplary implementation of marker delivery device 10 with respect to the flexible portion 30 of cannula 16, and more particularly shows a portion of an exemplary breast biopsy device 52 having the driver removed (not shown) that drives a cutter and vacuum unit in harvesting a tissue sample via a biopsy needle 54. Thereafter, cannula 16 of marker delivery device 10 is inserted through the lumen of biopsy needle 54 for placing tissue marker 12 in the tissue of the patient.

Biopsy needle 54 has a side sample notch 56 leading to a sample chamber 58 located at the lumen of biopsy needle 54. As cannula 16 is advanced in the lumen of biopsy needle 54 to the end of sample chamber 58, a ramped surface 58-1 at the end of sample chamber 58 exerts force (F) to deflect the distal end 16-2 of cannula 16 resulting in a flexure of flexible portion 30 of cannula (see also FIGS. 4A-4C), thereby exposing the distal end 16-2 of cannula 16 to sample notch 56. With a further advancement of cannula 16 in the lumen of biopsy needle 54, as shown in FIG. 8, the distal end 16-2 of cannula 16 extends through sample notch 56 to penetrate tissue adjacent the biopsy site.

Thereafter, an advancement of marker introducer rod 18 in lumen 16-4 of cannula 16 (see, e.g., FIG. 3) causes tissue marker 12 to be deployed into the tissue surrounding the biopsy site. Flexible region 50 of marker introducer rod 18 (see, e.g., FIG. 7) conforms to the shape of flexible portion 30 of cannula 16, before, during and after the flexure of flexible portion 30 of cannula 16.

Alternatively, the distal end 16-2 of cannula 16 may be exposed to sample notch 56 without extending though sample notch 56, and tissue marker 12 may be deployed though sample notch 56 of biopsy needle 54 into the biopsy cavity.

Referring again to FIGS. 1-3, deployment mechanism 20 is mounted to housing 24 of handle 14 and is configured to displace marker introducer rod 18 for deploying tissue marker 12 upon an actuation of deployment mechanism 20 by the user. In general, deployment mechanism 20 is configured to limit marker delivery device 10 to a single use for marker deployment. FIGS. 1 and 2 show deployment mechanism 20 in an initial position 60 (marker not deployed) and FIG. 3 shows deployment mechanism 20 in a marker deployed position 62.

More particularly, deployment mechanism 20 includes an introducer rod guide block 64, a marker deployment trigger 66, and a first shear member 68. Introducer rod guide block 64 is fixedly attached to the actuation end 18-1 of marker introducer rod 18, such as by molding a portion of marker introducer rod 18 into introducer rod guide block 64, and is slidably disposed in chamber 26 of housing 24. Marker deployment trigger 66 is accessible at an exterior of housing 24 of handle 14. Marker deployment trigger 66 is mounted to housing 24 for siding movement along trigger slot 24-5 of housing 24 from the initial position 60 shown in FIGS. 1 and 2 toward the front end 24-1 of housing 24 to position deployment mechanism 20 at the marker deployed position 62.

In the present embodiment, marker deployment trigger 66 and introducer rod guide block 64 are linked by first shear member 68. First shear member 68 extends from marker deployment trigger 66 and resides in a recess 70 located in introducer rod guide block 64. Thus, an actuation of marker deployment trigger 66 causes first shear member 68 to displace introducer rod guide block 64, which in turn displaces marker introducer rod 18 along the lengthwise extent 28 of cannula 16 to deploy tissue marker 12 from lumen 16-4 of cannula 16. First shear member 68 has a region of reduced cross section dimension 68-1, e.g., an annular groove, to provide a shear location.

An outer contour of introducer rod guide block 64 may be selected to be slidably received in a like-inner contour of longitudinal chamber 26 of housing 24 of handle 14. Accordingly, in embodiments where the outer contour of introducer rod guide block 64 and the like-inner contour of longitudinal chamber 26 are non-circular, introducer rod guide block 64 prevents rotation of marker introducer rod 18 with respect to housing 24 of handle 14, thus maintaining a constant orientation of marker introducer rod 18 relative to handle 14.

Also, in embodiments where the outer contour of introducer rod guide block 64 and the like-inner contour of longitudinal chamber 26 are circular, recess 70 of introducer rod guide block 64 may be in the form of a circumferential groove to facilitate a change in angular position, i.e., rotation, of marker introducer rod 18 with respect to housing 24 of handle 14. In such case, a rotator, e.g., knob, (not shown) positioned external to handle 14 may be coupled to introducer rod guide block 64 to effect a change in orientation of marker introducer rod 18 relative to handle 14.

As best shown in FIG. 2, deployment mechanism 20 may further include a lock mechanism 72 to lock marker deployment trigger 66 in the marker deployed position 62 after tissue marker 12 has been deployed. In the present embodiment, lock mechanism 72 includes a first lock member 72-1 formed on, or attached to, marker deployment trigger 66 and includes a second lock member 72-2 formed on, or attached to, housing 24. In operation, first lock member 72-1 permanently engages second lock member 72-2 when marker deployment trigger 66 is positioned in the marker deployed position 62, thereby limiting marker delivery device 10 to a single marker deployment operation.

One of first lock member 72-1 and second lock member 72-1 may be, for example, a lock channel and the other of first lock member 72-1 and second lock member 72-2 may be a spring-loaded insert member that engages the lock channel when marker deployment trigger 66, and in turn marker introducer rod 18, is positioned in marker deployed position 62. In the present embodiment shown in FIG. 2, for example, first lock member 72-1 is formed as a lock channel in marker deployment trigger 66, and second lock member 72-2 is in the form of a spring-loaded pin that engages the lock channel when marker deployment trigger 66 is slid toward the front end 24-1 of housing 24 to position deployment mechanism 20, and in turn marker introducer rod 18, in marker deployed position 62. As a further example, when second lock member 72-2 is formed as a lock channel in housing 24, the lock channel may be formed by, or integral with, trigger slot 24-5, and first lock member 72-1 as a spring-loaded insert member may be a cantilevered arm having a protrusion that engages the lock channel when marker deployment trigger 66 is positioned in marker deployed position 62.

Again referring to FIGS. 1-3, retraction mechanism 22 is mounted to housing 24 of handle 14 and is configured to facilitate a complete retraction of both cannula 16 and marker introducer rod 18 into chamber 26 of housing 24 of handle 14 upon an actuation of retraction mechanism 22 by the user, which most likely will occur following deployment of tissue marker 12. Retraction mechanism 22 is configured to prevent cannula 16 and marker introducer rod 18 from extending outside chamber 26 of housing 24 of handle 14 after the complete retraction of cannula 16 and marker introducer rod 18 into chamber 26, thus facilitating the safe disposal of marker delivery device 10, and alleviating concern about the accidental puncturing of medical personnel, or the patient, following the use of marker delivery device 10.

More particularly, retraction mechanism 22 includes a retraction trigger 74, a cannula guide block 76, a second shear member 78, and a spring 80. Retraction trigger 74 may be in the form of a push button that is accessible at the exterior of the housing 24, e.g., through a hole 24-7 in side wall 24-3. Cannula guide block 76 is fixedly attached to the proximal end 16-1 of cannula 16, such as by molding a portion of cannula 16 into cannula guide block 76. Cannula guide block 76 is slidably disposed in longitudinal chamber 26 of housing 24. In the present embodiment, second shear member 78 is formed as an extension of retraction trigger 74.

As best shown in FIG. 3, retraction trigger 74 and cannula guide block 76 are linked by second shear member 78 that is resident in a recess 82 located in cannula guide block 76, thus holding cannula guide block 76 stationary, e.g., axially stationary, relative to housing 24 of handle 14. Spring 80 is located between the front end 24-1 of housing 24 and cannula guide block 76, with spring 80 being in a compressed state prior to actuation of retraction trigger 74, thus providing a preload on cannula guide block 76.

An outer contour of cannula guide block 76 may be selected to be slidably received in an inner like-contour of longitudinal chamber 26 of housing 24 of handle 14. Accordingly, in embodiments where the outer contour of cannula guide block 76 and the inner like-contour of longitudinal chamber 26 are non-circular, cannula guide block 76 prevents rotation of cannula 16 with respect to housing 24 of handle 14, thus maintaining a constant orientation of cannula 16 relative to handle 14.

However, in embodiments where the outer contour of cannula guide block 76 and the inner like-contour of longitudinal chamber 26 are circular, recess 82 of cannula guide block 76 may be in the form of a circumferential groove to facilitate a change in angular position, i.e., rotation, of cannula 16 with respect to housing 24 of handle 14, thus facilitating a changeable orientation of cannula 16 relative to handle 14. In such case, cannula 16 may be manually rotated by grasping cannula 16 and turning. Alternatively, a rotator, e.g., knob, (not shown) positioned external to handle 14 may be coupled to guide block 76 to effect a change in orientation of cannula 16 relative to handle 14.

An actuation of retraction trigger 74 causes a complete retraction of both cannula 16 and marker introducer rod 18 into chamber 26 of housing 24 of handle 14. More particularly, as shown in FIG. 3, second shear member 78 has a region of reduced cross section dimension 78-1, e.g., an annular groove, to provide a shear location. Initially, the region of reduced cross section dimension 78-1 of second shear member 78 is contained within the hole 24-7 formed in side wall 24-3, thereby providing additional support at the region of reduced cross section dimension 78-1.

Figure 9:
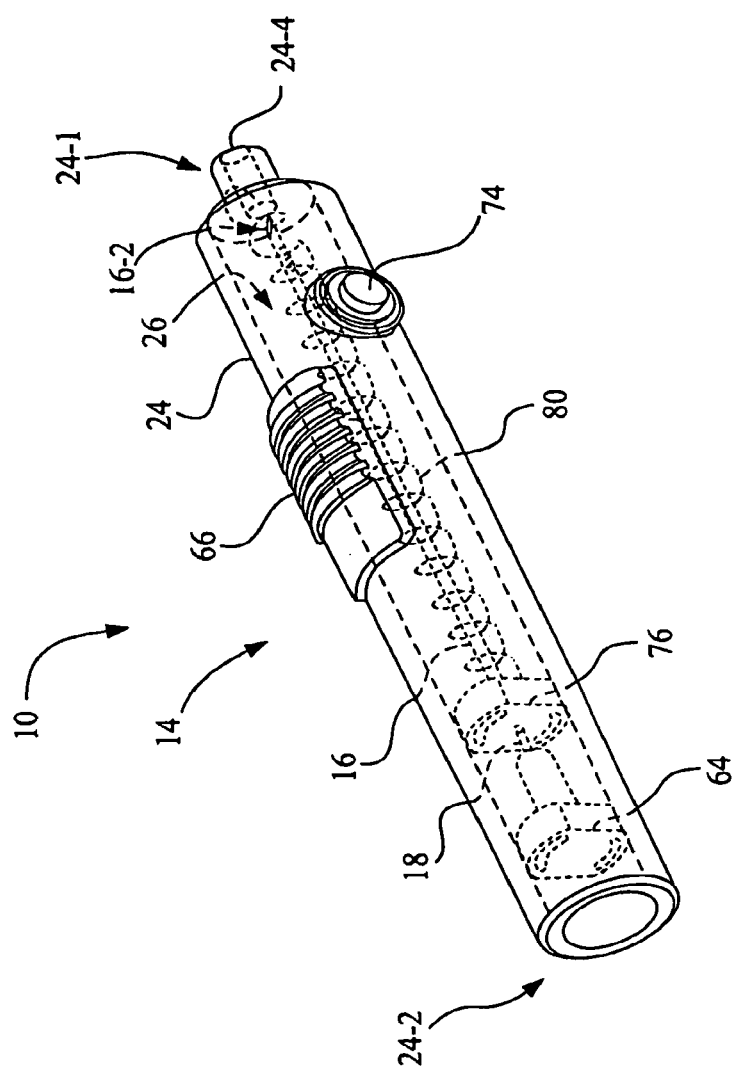
FIG. 9 is a perspective view of the marker delivery device of FIG. 1 following complete retraction of the cannula and marker introducer rod into the longitudinal chamber of the housing of the handle.

In the present embodiment, an actuation (depressing) of retraction trigger 74 radially displaces second shear member 78 causing second shear member 78 to shear. More particularly, by depressing retraction trigger 74, the region of reduced cross section dimension 78-1 of second shear member 78 enters longitudinal chamber 26 through side wall 24-3 of housing 24, such that the region of reduced cross section dimension 78-1 of second shear member 78 is no longer supported by side wall 24-3, and whereby the spring force exerted by spring 80 overcomes the shear resistance of the region of reduced cross section dimension 78-1 of second shear member 78. The shearing of second shear member 78 results in a release of spring 80 from the compressed state shown in FIGS. 1-3 to force cannula guide block 76 to move toward the back end 24-2 of housing 24 to begin an initial retraction of cannula 16, and wherein a continued decompression of spring 80 causes cannula guide block 76 to impact introducer rod guide block 64 to shear first shear member 68, whereby beginning a simultaneous retraction of both cannula 16 and marker introducer rod 18 into chamber 26 of housing 24 of handle 14. The simultaneous retraction of both cannula 16 and marker introducer rod 18 into handle 14 terminates after both cannula 16 and marker introducer rod 18 are completely contained in longitudinal chamber 26 of housing 24 of handle 14, as illustrated in FIG. 9.

Alternatively, a spacing device 84 (see FIG. 1) may be positioned between introducer rod guide block 64 and cannula guide block 76. Spacing device 84 has a length along the lengthwise extent 28 such that cannula guide block 76 is in operable contact with introducer rod guide block 64 when introducer rod guide block 64 is positioned in the marker deployed position 62, such that first shear member 68 and second shear member 78 are sheared substantially simultaneously when retraction trigger 74 displaced, resulting in a complete simultaneous retraction of both cannula 16 and marker introducer rod 18 into chamber 26 of housing 24.

FIGS. 10-15 depict another embodiment of the invention, depicting a marker delivery device 110 that includes a handle 112, cannula 16, marker introducer rod 18, a deployment mechanism 114 and a cannula retraction mechanism 116. Cannula 16 and marker introducer rod 18 may be configured as previously described, and thus for brevity the full details of their operation will not be repeated here. Marker delivery device 110 functionally differs from the embodiment of marker delivery device 10, in that deployment mechanism 114 of marker delivery device 110 may be configured to facilitate a full retraction of marker introducer rod 18 prior to beginning the retraction of cannula 16 effected by cannula retraction mechanism 116.

Handle 112 is configured of an appropriate size and shape to be grasped by the hand of the user of marker delivery device 110. Handle 112 includes a housing 118 having a front end 118-1, a back end 118-2 and a side wall 118-3, with a longitudinal chamber 120 located between front end 118-1 and back end 118-2 that is surrounded by side wall 118-3. A hole 118-4 leads from longitudinal chamber 120 through the front end 118-1 of housing 118 to the exterior of handle 112. Cannula 16 is positioned in handle 112 such that cannula 16 initially extends through hole 118-4 beyond the front end 118-1 of housing 118 prior to marker deployment. A trigger slot 118-5 extends through side wall 118-3 of housing 118.

Figure 10:
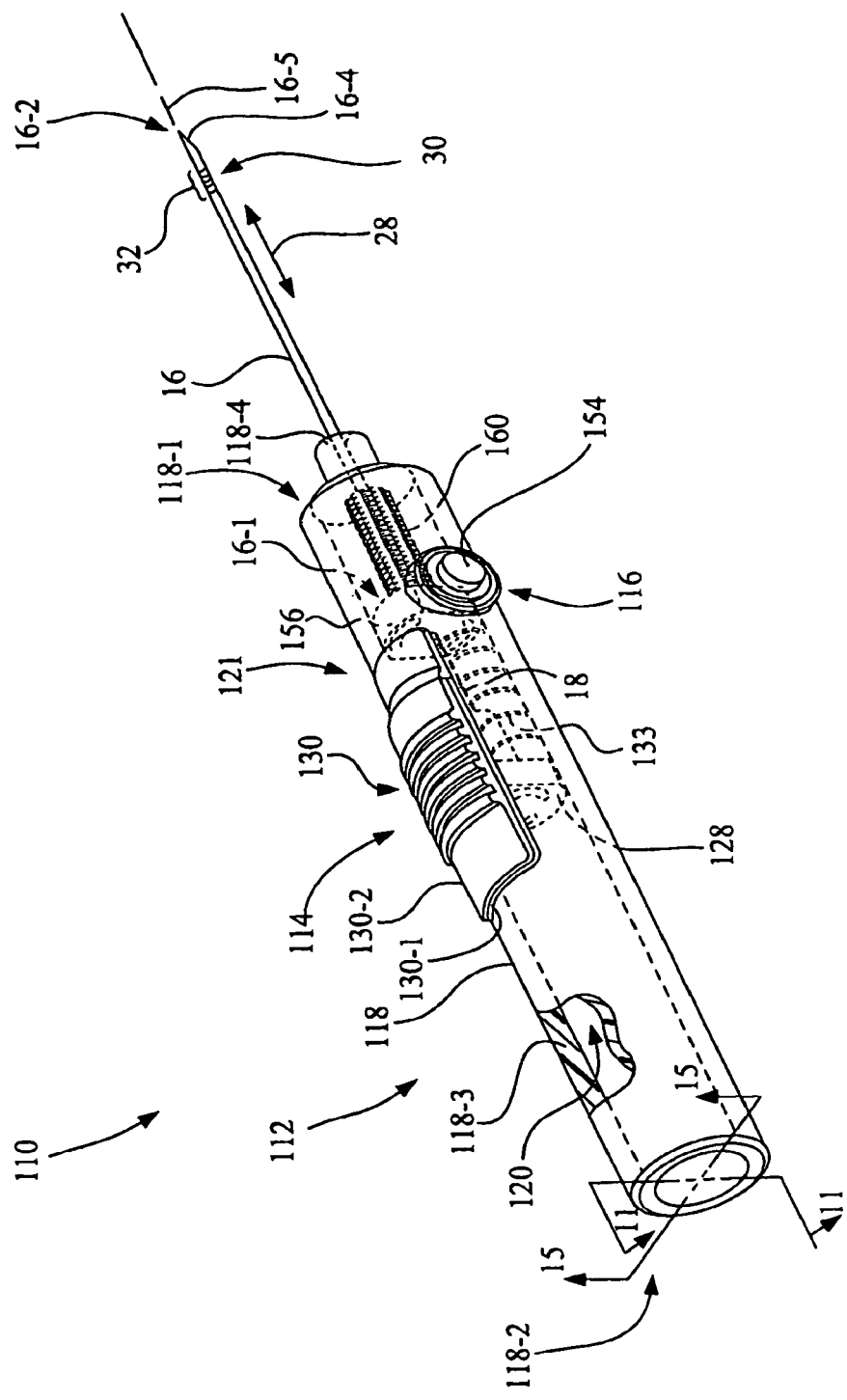
FIG. 10 is a perspective view of a marker delivery device configured for deploying a tissue marker in accordance with another embodiment of the present invention.
Figure 11:
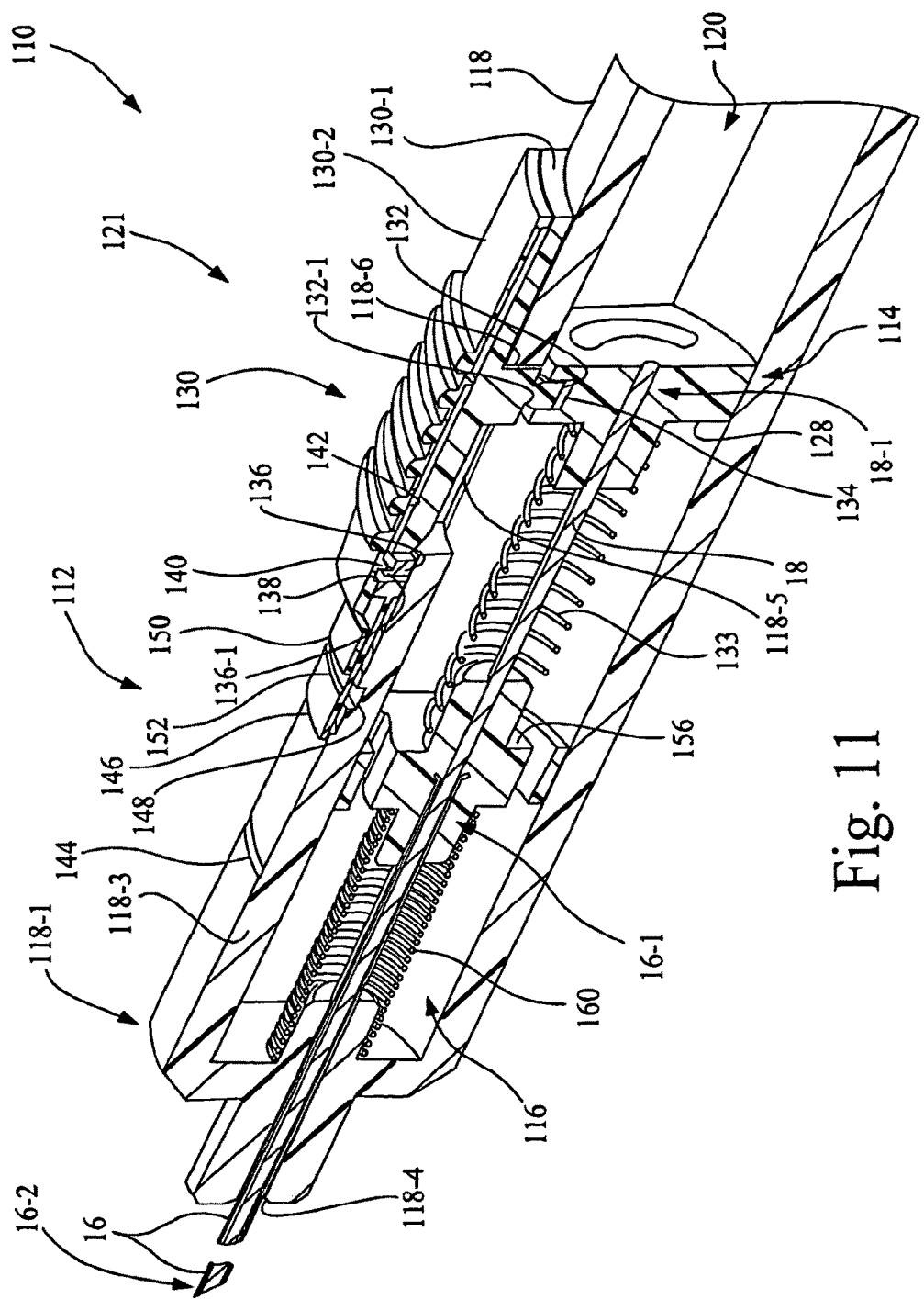
FIG. 11 is a section view of the marker delivery device of FIG. 10 taken along plane 11-11, showing the deployment mechanism in an initial position.
Figure 12:
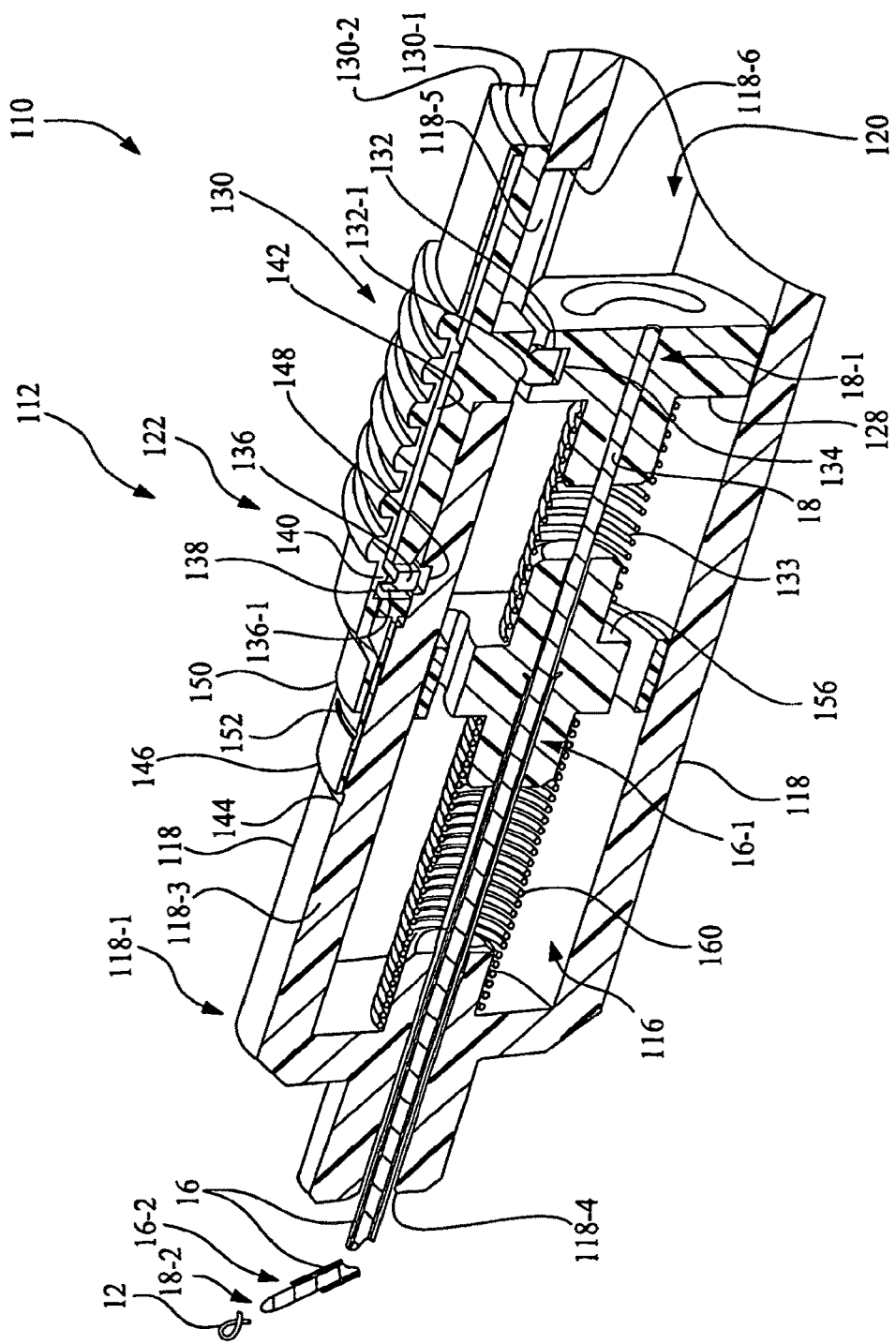
FIG. 12 is a section view of the marker delivery device of FIG. 10, showing the deployment mechanism in a marker deployed position.
Figure 13:
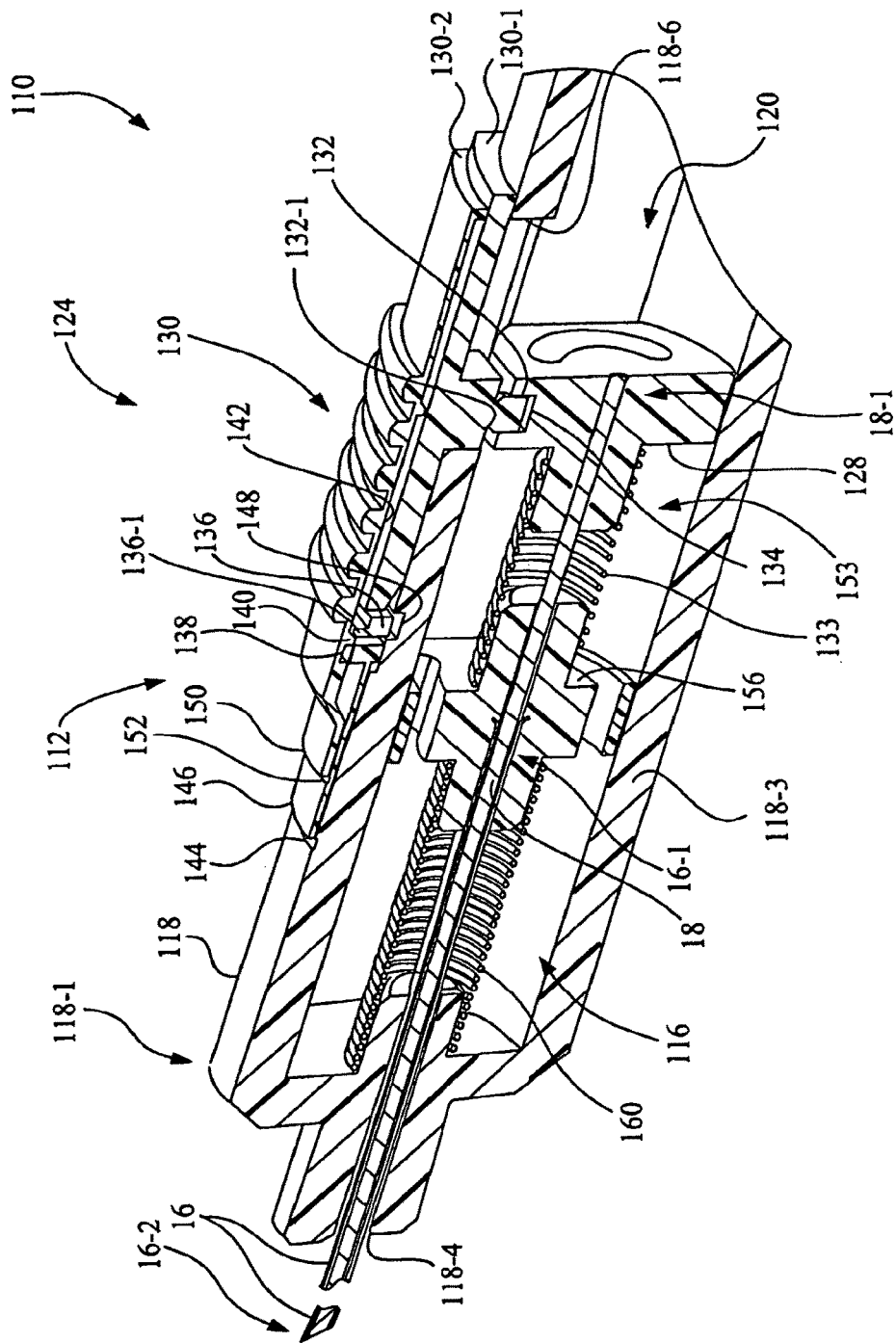
FIG. 13 is a section view of the marker delivery device of FIG. 10, showing the deployment mechanism in a marker introducer rod initial retraction position.
Figure 14:
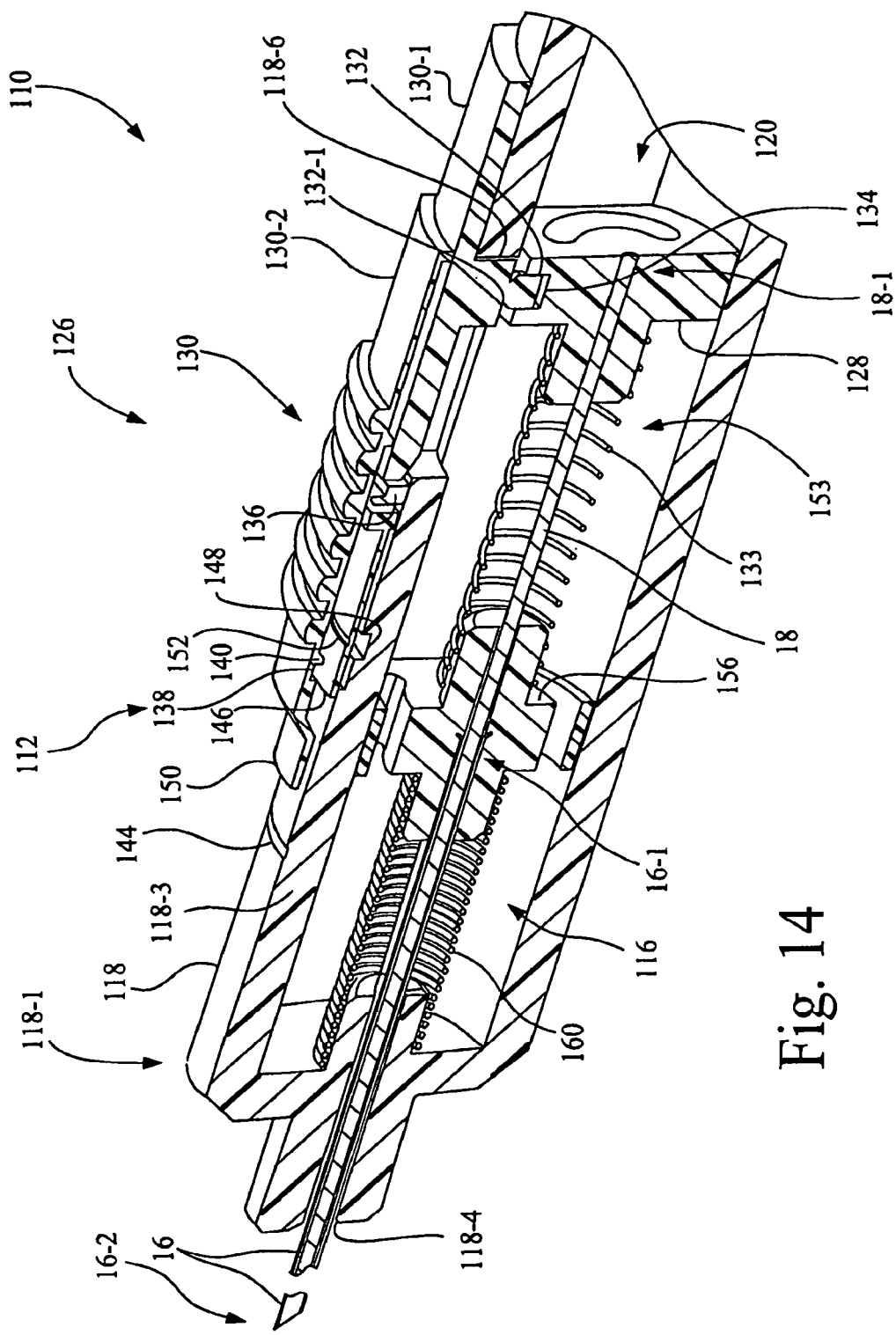
FIG. 14 is a section view of the marker delivery device of FIG. 10, showing the deployment mechanism in a marker introducer rod post-initial retraction position.

Deployment mechanism 114 is mounted to housing 118 of handle 112 and is configured to displace marker introducer rod 18 for deploying tissue marker 12 upon an actuation of deployment mechanism 114 by the user. FIGS. 10 and 11 show deployment mechanism 114 in an initial position 121 (unused, marker not deployed), FIG. 12 shows deployment mechanism 114 in a marker deployed position 122, FIG. 13 shows deployment mechanism 114 in a marker introducer rod initial retraction position 124, and FIG. 14 shows deployment mechanism 114 in a marker introducer rod post-initial retraction position 126.

Deployment mechanism 114 includes an introducer rod guide block 128, a multi-stage marker deployment trigger 130, a first shear member 132, and an introducer rod retraction spring 133. First shear member 132 has a region of reduced cross section dimension 132-1, e.g., an annular groove, to provide a shear location. Introducer rod guide block 128 is attached to the actuation end 18-1 of marker introducer rod 18, and is slidably disposed in longitudinal chamber 120 of housing 118. Marker deployment trigger 130 is accessible at an exterior of housing 118 of handle 112. Marker deployment trigger 130 includes an inner sleeve 130-1 and an outer actuator 130-2. Marker deployment trigger 130 is mounted to housing 118 for siding movement along trigger slot 118-5.

FIGS. 11-14 show various stages of movement of inner sleeve 130-1 and an outer actuator 130-2 of marker deployment trigger 130. In the present embodiment, marker deployment trigger 130 and introducer rod guide block 128 are linked by first shear member 132. First shear member 132 extends from inner sleeve 130-1 of marker deployment trigger 130 and resides in a recess 134 located in introducer rod guide block 128.

Initially, as shown in FIG. 11, inner sleeve 130-1 and outer actuator 130-2 of marker deployment trigger 130 are linked by a drive tab 136 mounted to inner sleeve 130-1 that engages a drive slot 138 formed in outer actuator 130-2, so that inner sleeve 130-1 and outer actuator 130-2 initially move concurrently. Drive slot 138 is defined by a downward facing lip 140 that separates drive slot 138 from an elongate introducer rod retraction slot 142. Drive tab 136 may be hinge-mounted, e.g., by a linking membrane, to inner sleeve 130-1. Drive tab 136 includes an upwardly extending protrusion 136-1 that is initially engaged with lip 140 in drive slot 138. Introducer rod retraction spring 133 is positioned between cannula retraction mechanism 116 and introducer rod guide block 128 under slight compression, and more particularly, between introducer rod guide block 128 and cannula guide block 156.

Referring to FIG. 12, an actuation of marker deployment trigger 130 by sliding outer actuator 130-2 of marker deployment trigger 130 toward the front end 118-1 of housing 118 of handle 112 causes inner sleeve 130-1 to move first shear member 132 longitudinally along longitudinal chamber 120 to displace introducer rod guide block 128, which in turn displaces marker introducer rod 18 along the lengthwise extent 28 of cannula 16 to deploy tissue marker 12 from lumen 16-4 of cannula 16 when the marker deployed position 122 depicted in FIG. 12 is reached. At this stage, introducer rod retraction spring 133 is being compressed. Housing 118 includes an indicator line 144, such that when a leading edge 146 of inner sleeve 130-1 aligns with indicator line 144 to indicate that the marker deployed position 122 has been reached, the user is assured of a complete deployment of tissue marker 12 out of the distal end 16-2 of cannula 16.

Also, as depicted in FIG. 12, when marker deployment trigger 130 is positioned at marker deployed position 122, drive tab 136 is positioned over a retraction channel 148 in housing 118. A further sliding of outer actuator 130-2 of marker deployment trigger 130 toward the front end 118-1 of housing 118 of handle 112 causes lip 140 forming a trailing edge of drive slot 138 to force protrusion 136-1 of drive tab 136 to twist forward into a deformation downward into a retraction channel 148 formed in housing 118 of handle 112, thereby allowing lip 140 to begin to pass over protrusion 136-1 of drive tab 136. At this stage, introducer rod retraction spring 133 has reached maximum compression.

As depicted in FIG. 13, the further sliding of outer actuator 130-2 of marker deployment trigger 130 toward the front end 118-1 of housing 118 of handle 112 causes lip 140 to pass over the upward protrusion 136-1 of drive tab 136, thereby allowing drive tab 136 to regain its original geometry with respect inner sleeve 130-1, thereby moving upwardly out of retraction channel 148. This action occurs when the leading edge 150 of outer actuator 130-2 aligns with indicator line 152 of inner sleeve 130-1. At this stage, introducer rod retraction spring 133 starts to decompress. Accordingly, a portion of deployment mechanism 114, e.g., inner sleeve 130-1, outer actuator 130-2, drive tab 136, lip 140, and retraction channel 148 of deployment mechanism 114, also functions as an introducer rod retraction mechanism 153 for marker introducer rod 18.

As depicted in FIG. 14, with upward protrusion 136-1 of drive tab 136 fully released from retraction channel 148 and upward protrusion 136-1 of drive tab 136 being positioned in introducer rod retraction slot 142, the decompression of introducer rod retraction spring 133 forces introducer rod guide block 128 toward the back end 118-2 of housing 118 (see FIG. 10), and in turn marker introducer rod 18 and inner sleeve 130-1 are returned toward their initial positions as depicted in FIGS. 10 and 11. The spring force provided by introducer rod retraction spring 133 may be selected, for example, such that the impact of inner sleeve 130-1 with end wall 118-6 of housing 118 causes first shear member 132 to shear at the region of reduced cross section dimension 132-1, thereby facilitating a complete retraction of marker introducer rod 18 into longitudinal chamber 120, prior to initiating retraction of cannula 16.

Alternatively, the spring force provided by introducer rod retraction spring 133 may be selected, for example, such that the impact of inner sleeve 130-1 with end wall 118-6 of housing 118 stops the retraction of marker introducer rod 18 into longitudinal chamber 120 after a partial retraction of marker introducer rod 18, prior to initiating retraction of cannula 16.

Also, as depicted in FIG. 14, at this stage outer actuator 130-2 of marker deployment trigger 130 is no longer linked to inner sleeve 130-1. Thus, a subsequent extension of marker introducer rod 18 by actuation of outer actuator 130-2 of marker deployment trigger 130 is prevented, thereby rendering marker delivery device 110 usable for only a single tissue marker deployment.

Figure 15:
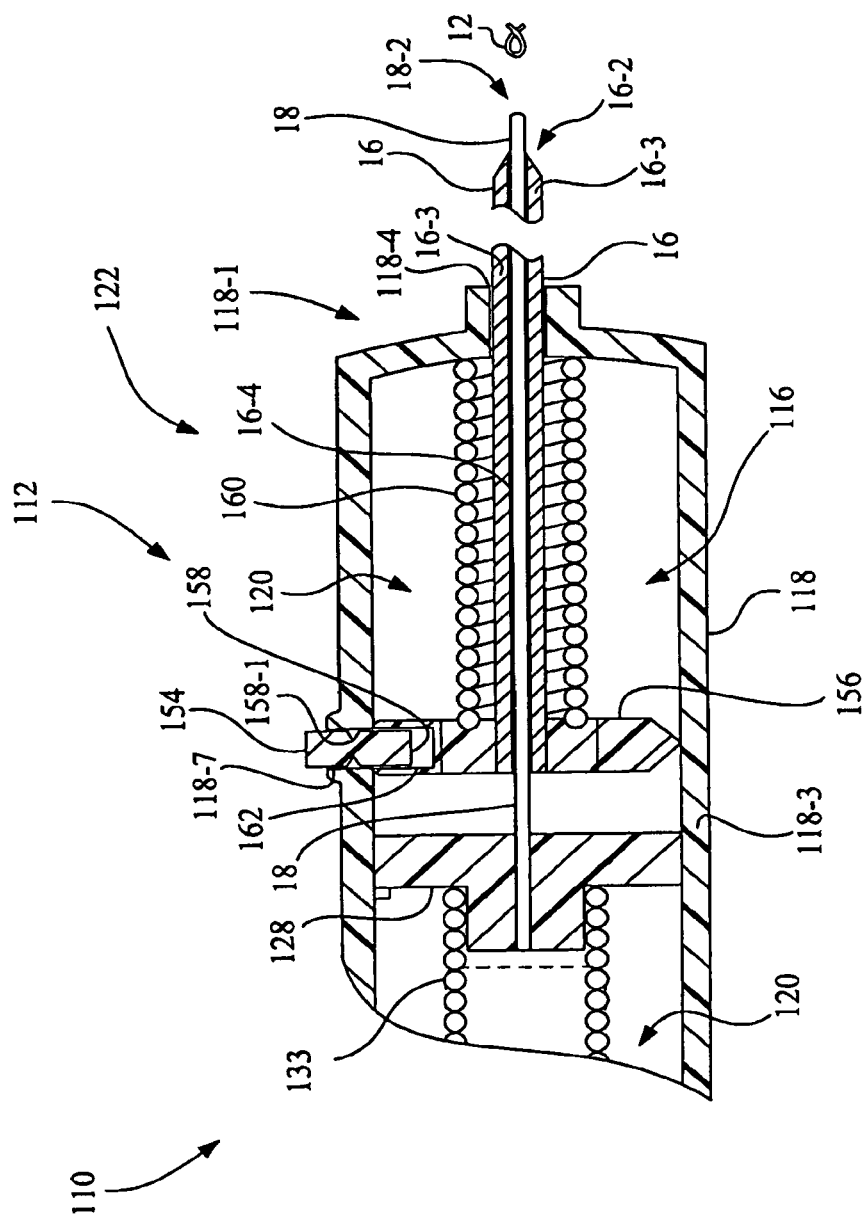
FIG. 15 is a section view of a portion of the marker delivery device of FIG. 10 taken along plane 15-15, depicting the cannula retraction mechanism.

Referring again also to FIG. 10 in relation to FIGS. 14 and 15, cannula retraction mechanism 116 is mounted to housing 118 of handle 112 and is configured to facilitate a complete retraction of cannula 16 into longitudinal chamber 120 of housing 118 of handle 112 upon an actuation of cannula retraction mechanism 116 by the user, which most likely will occur following deployment of tissue marker 12. FIG. 15 shows cannula retraction mechanism 116, with marker introducer rod 18 in marker deployed position 122. Cannula retraction mechanism 116 is configured to prevent cannula 16 and marker introducer rod 18 from extending outside longitudinal chamber 120 of housing 118 of handle 112 after the complete retraction of cannula 16 and marker introducer rod 18 into longitudinal chamber 120, thus facilitating the safe disposal of marker delivery device 110, and alleviating concern about the accidental puncturing of medical personnel, or the patient, following the use of marker delivery device 110.

Cannula retraction mechanism 116 includes a retraction trigger 154, a cannula guide block 156, a second shear member 158, and a cannula retraction spring 160. Retraction trigger 154 may be in the form of a push button that is accessible at the exterior of housing 118, e.g., through a hole 118-7 in side wall 118-3. Cannula guide block 156 is attached to the proximal end 16-1 of cannula 16. Cannula guide block 156 is slidably disposed in longitudinal chamber 120 of housing 118. In the present embodiment, second shear member 158 is formed as an extension of retraction trigger 154.

Retraction trigger 154 and cannula guide block 156 are linked by second shear member 158 that is resident in a recess 162 located in cannula guide block 156, thus holding cannula guide block 156 stationary relative to housing 118 of handle 112. Cannula retraction spring 160 is located between the front end 118-1 of housing 118 and cannula guide block 156, with cannula retraction spring 160 being in a compressed state prior to actuation of retraction trigger 154, thus providing a preload on cannula guide block 156.

An actuation of retraction trigger 154 causes a complete retraction of cannula 16 into longitudinal chamber 120 of housing 118 of handle 112. More particularly, as shown in FIG. 15, initially, the region of reduced cross section dimension 158-1 of second shear member 158 is supported by side wall 118-3, thereby providing additional support at the region of reduced cross section dimension 158-1. An actuation (depressing) of retraction trigger 154 radially displaces second shear member 158 causing the region of reduced cross section dimension 158-1 of second shear member 158 to enter longitudinal chamber 120 through side wall 118-3 of housing 118, such that the region of reduced cross section dimension 158-1 of second shear member 158 is no longer supported by the side wall 118-3, and whereby the spring force exerted by cannula retraction spring 160 overcomes the shear resistance of the region of reduced cross section dimension 158-1 of second shear member 158. The shearing of second shear member 158 results in a release of cannula retraction spring 160 from the compressed state shown to force cannula guide block 156 to move toward the back end 118-2 of housing 118 to complete a full retraction of cannula 16 into longitudinal chamber 120 of housing 118 of handle 112.

In the event of a partial retraction of marker introducer rod 18, or in the event that the user does not perform the previously described retraction of marker reducer rod, into longitudinal chamber 120 of housing 118 of handle 112 prior to actuation of retraction trigger 154 (as depicted in FIG. 15), the continued decompression of cannula retraction spring 160 causes cannula guide block 156 to impact introducer rod guide block 128 to shear first shear member 132, whereby facilitating a full simultaneous retraction of both cannula 16 and marker introducer rod 18 into longitudinal chamber 120 of housing 118 of handle 112.

The retraction process is completed when both cannula 16 and marker introducer rod 18 are completely contained in longitudinal chamber 120 of housing 118 of handle 112.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A marker delivery device configured for deploying a tissue marker, comprising:
    a handle including a housing having a front end, a back end, a side wall, a chamber located between the front end and the back end that is surrounded by the side wall, a first hole leading from the chamber to the exterior of the handle through the front end of the housing, and a second hole leading from the chamber to the exterior of the handle through the side wall of the housing;
    a cannula having a proximal end, a distal end, and a lumen, the cannula being positioned in the handle such that the cannula retractably extends through the first hole beyond the front end of the housing; and
    a retraction mechanism mounted to the housing, the retraction mechanism being coupled to the proximal end of the cannula, the retraction mechanism being configured to store a retraction force, and configured to facilitate a retraction of the cannula into the chamber of the housing of the handle upon an actuation of the retraction mechanism, the retraction mechanism including:
        a retraction trigger accessible at the exterior of the housing, the retraction trigger configured to be depressed by an exterior force in an axial direction toward the chamber of the housing of the handle;
        a shear member having a longitudinal length that is axially oriented relative to the housing of the handle, the longitudinal length having an exterior end and an interior end, the shear member having a shear region of reduced cross section dimension, and the shear region of reduced cross section being located between the exterior end and the interior end; and a cannula guide block attached to the proximal end of the cannula, the retraction force configured to be applied to the cannula guide block, the cannula guide block configured to be slidably disposed in the chamber of the housing, the retraction trigger configured to be linked to the cannula guide block by the shear member via the retraction trigger being coupled to the exterior end of the longitudinal length of the shear member and the cannula guide block being coupled to the interior end of the longitudinal length of the shear member, the retraction mechanism is configured to be in a ready position when the shear region of reduced cross section dimension of the shear member is supported by the side wall by being in alignment with the second hole of the housing of the handle; upon actuation of the retraction trigger, the shear region of reduced cross section dimension is configured to move out of alignment with the second hole and the shear member is configured to be sheared at the shear region of reduced cross section dimension by release of the retraction force upon the cannula guide block which transfers the retraction force to the interior end of the longitudinal length of the shear member to permanently disconnect the retraction trigger from the cannula guide block.

2. The marker delivery device of claim 1, wherein each of the exterior end and the interior end of the longitudinal length of the shear member has the same cross sectional dimension.

3. The marker delivery device of claim 1, wherein the shear region of reduced cross section dimension is an annular groove.

* * * * *